(12) United States Patent
Ooe et al.

(10) Patent No.: US 7,537,904 B1
(45) Date of Patent: May 26, 2009

(54) CELL FOR MEASURING THE ABILITY TO CONTROL THE ACTIVITY OF A LIGAND-RESPONSIVE TRANSCRIPTION CONTROL FACTOR

(75) Inventors: Norihisa Ooe, Osaka (JP); Haruyuki Matsunaga, Osaka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/550,173

(22) Filed: Apr. 14, 2000

(30) Foreign Application Priority Data

| Apr. 14, 1999 | (JP) | ................................. 11-106791 |
| Apr. 14, 1999 | (JP) | ................................. 11-106792 |
| Apr. 14, 1999 | (JP) | ................................. 11-106793 |
| Apr. 15, 1999 | (JP) | ................................. 11-107774 |

(51) Int. Cl.
*G01N 33/566* (2006.01)
*C12N 5/00* (2006.01)
*C12N 5/06* (2006.01)
*C12N 5/08* (2006.01)

(52) U.S. Cl. ...................... 435/7.21; 435/325; 435/367; 435/371; 435/357

(58) Field of Classification Search ................ 536/23.1, 536/24.1; 435/6, 455, 325; 11/11
See application file for complete search history.

(56) References Cited

U.S. PATENT DOCUMENTS

| 5,071,773 | A |   | 12/1991 | Evans et al. |
| 5,298,429 | A | * | 3/1994  | Evans et al. ................. 436/501 |
| 5,312,732 | A |   | 5/1994  | Evans et al. |
| 5,378,822 | A |   | 1/1995  | Bradfield et al. |
| 5,512,483 | A | * | 4/1996  | Mader et al. ............. 435/320.1 |
| 5,534,418 | A |   | 7/1996  | Evans et al. |
| 5,597,705 | A |   | 1/1997  | Evans et al. |
| 5,606,021 | A |   | 2/1997  | Evans et al. |
| 5,650,283 | A | * | 7/1997  | Bradfield et al. ............. 435/7.1 |
| 5,811,231 | A |   | 9/1998  | Farr et al. |
| 5,834,213 | A | * | 11/1998 | O'Malley et al. ............ 435/7.8 |
| 5,854,010 | A |   | 12/1998 | Denison et al. |
| 6,117,638 | A | * | 9/2000  | Kushner et al. ................ 435/6 |

FOREIGN PATENT DOCUMENTS

| WO | WO 95/06754 A1 | 3/1995 |
| WO | WO 96/30505 A1 | 10/1996 |

OTHER PUBLICATIONS

Wigler et al. Cell 16:777-785 1979.*
Deans et al. Proceedings of the National Academy of Science USA 81:1292-1296 1984.*
Alan S. Waldman et al, Stable Transfection of Mammalian Cells by Syringe-Mediated Mechanical Loading of DNA, Analytical Biochemistry 258, 216-222 1998, Article No. AB 982605.*
Waldman, AS & Waldman, BC Stable Transfection of Mammalian Cells by Syringe-Mediated Mechanical Loading of DNA, Analytical Biochemistry 258:216-222, 1998.*
GenBank Accession Entry J00895.*
GenBank Acession Entry J00605.*
Carter et al. Duplicated Heavy Metal Control Sequence of the Mouse Metallothionein-I Gene, Proc. Natl. Acad. Sci. USA, 81:7392-7396, 1984.*
Zhang D, Trudeau VL. Integration of membrane and nuclear estrogen receptor signaling. Comp Biochem Physiol A Mol Integr Physiol: Jul. 2006;144(3):306-15. Epub Mar. 3, 2006.*
M.S. Denison et al.; Toxicology and Applied Pharmacology; vol. 152; No. 2; Oct. 1998; pp. 406-414; XP002106047.
Lawrence E. Heisler et al.; Molecular and Cellular Endocrinology; vol. 126; No. 1; 1997; pp. 59-73; XP002258410.
Joseph Ostby et al.; Toxicology and Industrial Health; vol. 15; No. 1-2; Jan. 1999; pp. 80-93; XP008023498.
Anne Rentoumis et al.; Molecular Endocrinology; vol. 4; No. 10, 1990; pp. 1522-1531; XP008023532.
Momoyo Kubota et al.; Journal of Biochemistry; vol. 110; No. 2; 1991; pp. 232-236; XP008023497.
Masako Izumi et al.; Experimental Cell Research; vol. 197; 1991; pp. 229-233; XP000196772.

(Continued)

*Primary Examiner*—Nancy Vogel
(74) *Attorney, Agent, or Firm*—Birch, Stewart, Kolasch & Birch, LLP

(57) ABSTRACT

The present invention provides an animal cell expressing a gene coding a ligand-responsive transcription control factor and securely maintaining a DNA comprising in a molecule, the following genes (a) and (b):

(a) a reporter gene connected downstream from a transcription control region, in which said transcription control region substantially consists of a recognition sequence of said ligand-responsive transcription control factor and a minimum promoter which can function in said cell; and (b) a selective marker gene which can function in said cell; provided that the following gene (c):

(c) a reporter gene connected downstream from a promoter which transcription activity is unchanged by having said responsive transcription control factor contacted with a ligand of said ligand-responsive transcription control factor, said reporter gene (c) coding a protein which can be differentiated from the protein coded by said gene (a) is not present in said cell and the like.

The cell in the present invention is a cryopreservable cell which can be used to measure the action of a chemical substance over the transcription control ability of a ligand-responsive transcription control factor.

13 Claims, 4 Drawing Sheets

OTHER PUBLICATIONS

James L. O'Conner et al.; Steroids; vol. 64; No. 9; Sep. 1999; pp. 592-597; XP002258411.

Hoffman, et al., Cloning of a Factor Required . . . , *Science*, vol. 252, May 1991, pp. 954-958.

Dolwick, et al., Cloning and Expression . . . , *Mol. Pharmacol.*, vol. 44, 1993, pp. 911-917.

Burbach, et al., Cloning of the Ah-receptor . . . , *Proc. Natl. Acad. Sci. USA*, vol. 89, Sep. 1992, pp. 8185-8189.

Carver, et al., Tissue specific expression of . . . , *Nucleic Acids Res.*, vol. 22, No. 15, 1994, pp. 3038-3044.

Hollenberg, et al., Primary structure and expression . . . , *Nature*, vol. 318, Dec. 1985, pp. 635-641.

Mukherjee, et al., Human and Rat Peroxisome . . . , *J. Steroid Biochem Molec. Biol.*, vol. 51., No. 3/4, 1994, pp. 157-166.

Denison, et al., The DNA Recognition Site . . . , *J. Bio. Chem.*, vol. 263, No. 33, Nov. 1988, pp. 17221-17224.

Fujisawa-Sehara, et al., Characterization of xenobiotic responsive . . . , *Nucleic Acids Res.*, vol. 15, No. 10, 1987, pp. 4179-4191.

Rushmore, et al., Regulation of glutathione . . . , *Proc. Natl Acad. Sci. USA*, vol. 87, May 1990, pp. 3826-3830.

Umesono, et al., Determinants of Target Gene . . . , *Cell*, vol. 57, Jun. 1989, pp. 1139-1146.

Gouilleux, et al., Cooperation between structural . . . , *Nucleic Acids Res.*, vol. 19, No. 7, pp. 1563-1569.

Glass, C., Differential Recognition of Target . . . , *Endocrine Review*, vol. 15, No. 3, 1994, pp. 391-407.

Dierks, et al., DNA sequences preceding . . . , *Proc. Natl. Acad. Sci. USA*, vol. 78, No. 3, Mar. 1981, pp. 1411-1415.

\* cited by examiner

SEQUENCE LISTING

```
<160> NUMBER OF SEQ ID NOS: 34

<210> SEQ ID NO 1
<211> LENGTH: 6
<212> TYPE: DNA
<213> ORGANISM: Unknown Organism
<220> FEATURE:
<223> OTHER INFORMATION: Description of Unknown Organism: consensus
      sequence of a dioxin-responsive sequence
<221> NAME/KEY: Unsure
<222> LOCATION: (1)..(1)
<223> OTHER INFORMATION: n = t or a
<300> PUBLICATION INFORMATION:
<303> JOURNAL: J. Biol. Chem.
<304> VOLUME: 271
<306> PAGES: 3952-3958
<307> DATE: 1996-02-01

<400> SEQUENCE: 1 ngcgtg                                                               6

<210> SEQ ID NO 2
<211> LENGTH: 16
<212> TYPE: DNA
<213> ORGANISM: Unknown Organism
<220> FEATURE:
<223> OTHER INFORMATION: Description of Unknown Organism: consensus
      sequence of an estrogen-responsive sequence
<221> NAME/KEY: Unsure
<222> LOCATION: (7)..(9)
<223> OTHER INFORMATION: n = a,c,g,t any unknown or other.

<400> SEQUENCE: 2
```

```
aggtcannnt gacctt                                                    16
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer for
      PCR with human genomic DNA.

<400> SEQUENCE: 3

```
ttgagctagg cacgcaaata                                                20
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer for
      PCR with human genomic DNA

<400> SEQUENCE: 4

```
gctttgattg gcagagcaca                                                20
```

<210> SEQ ID NO 5
<211> LENGTH: 51
<212> TYPE: DNA
<213> ORGANISM: mouse
<220> FEATURE:
<223> OTHER INFORMATION: The sequence is composed of nucleotide
      sequences derived from a nucleotide sequence near the TATA
      box of a mouse metallothionein I gene. The
      sequence is introduced into mouse and human cells.

<400> SEQUENCE: 5

```
gatctcgact ataaagaggg caggctgtcc tcaagcgtca ccacgacttc a             51
```

<210> SEQ ID NO 6
<211> LENGTH: 52
<212> TYPE: DNA
<213> ORGANISM: mouse
<220> FEATURE:
<223> OTHER INFORMATION: The sequence is composed of nucleotide
      sequences derived from a nucleotide sequence near the TATA
      box of a mouse metallothionein I gene. The
      sequence is introduced into mouse and human cells.

<400> SEQUENCE: 6

```
agcttgaagt cgtggtgacg cttagaggac agcctgccct ctttatagtc ga            52
```

<210> SEQ ID NO 7
<211> LENGTH: 33
<212> TYPE: DNA
<213> ORGANISM: Xenopus
<220> FEATURE:
<223> OTHER INFORMATION: The sequence is located at the upstream of a
      Xenopus-derived vitellogenin gene containing a
      recognition sequence of an estrogen receptor. The
      sequence is introduced into mouse and human cells.

<400> SEQUENCE: 7

```
tcgacaaagt caggtcacag tgacctgatc aag                                 33
```

<210> SEQ ID NO 8
<211> LENGTH: 31
<212> TYPE: DNA
<213> ORGANISM: Artificial Sequence

```
<220> FEATURE:
<223> OTHER INFORMATION: Description of Artificial Sequence:primer for
      PCR with pTK beta

<400> SEQUENCE: 8
cggcagatct tctttagttc tatgatgaca c                              31

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:primer for
      PCR with pTK beta

<400> SEQUENCE: 9
cggaagcttg atctgcggca cgctgttga                                 29

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 10
cctgcgggga cacggtctgc accctgcccg cggcc                          35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 11
cagggagctc tcagactgtg gcagggaaac cctct                          35

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 12
cccagccacc atgaccatga ccctccacac caaagcatct                     40

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 13
cagggagctc tcagactgtg gcagggaaac cctct                          35

<210> SEQ ID NO 14
<211> LENGTH: 35
<212> TYPE: DNA
<213> ORGANISM: Artificial Sequence
<220> FEATURE:
```

```
<223> OTHER INFORMATION: Description of Artificial Sequence:primer for
      PCR with human cDNA

<400> SEQUENCE: 14
ttgagttact gagtccgatg aatgtgcttg ctctg                               35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 15
aaatgaggga ccacacagca gaaagatgaa gccca                               35

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 16
gccgcggccg cccagccacc atggatataa aaaactcacc atctagcctt aattc         55

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 17
gggtctagaa atgagggacc acacagcaga aagatgaagc cca                      43

<210> SEQ ID NO 18
<211> LENGTH: 52
<212> TYPE: DNA
<213> ORGANISM: mouse
<220> FEATURE:
<223> OTHER INFORMATION: The sequence is derived from a nucleotide
      sequence near the TATA box of a mouse metallothionein I
      gene. The sequence is used for human cells. The
      sequence is introduced into human cells.

<400> SEQUENCE: 18
gatctcgact ataaagaggg caggctgtcc tctaagcgtc accacgactt ca            52

<210> SEQ ID NO 19
<211> LENGTH: 52
<212> TYPE: DNA
<213> ORGANISM: mouse
<220> FEATURE:
<223> OTHER INFORMATION: The sequence is derived from a nucleotide
      sequence near the TATA box of a mouse metallothionein I
      gene. The sequence is used for human cells. The
      sequence is introduced into human cells.

<400> SEQUENCE: 19
agcttgaagt cgtggtgacg cttagaggac agcctgccct ctttatagtc ga            52

<210> SEQ ID NO 20
<211> LENGTH: 35
```

```
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 20
gaggcggggt aagggaagta ggtggaagat tcagc                              35

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 21
gggtggggaa atagggtttc caatgcttca ctggg                              35

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 22
cccagccacc atggaagtgc agttagggct gggaagggtc                         40

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 23
gggtggggaa atagggtttc caatgcttca ctggg                              35

<210> SEQ ID NO 24
<211> LENGTH: 38
<212> TYPE: DNA
<213> ORGANISM: mammal
<220> FEATURE:
<223> OTHER INFORMATION: The sequence is containing a recognition
      sequence (TRE) of a thyroid receptor. The sequence is
      introduced into human cells.

<400> SEQUENCE: 24 caagggatc cagcttgacc tgacgtcagg tcaagtcg                            38

<210> SEQ ID NO 25
<211> LENGTH: 52
<212> TYPE: DNA
<213> ORGANISM: mouse
<220> FEATURE:
<223> OTHER INFORMATION: The sequence is derived from a nucleotide
      sequence near the TATA box of a mouse metallothionein I
      gene. The sequence is introduced into human cells.

<400> SEQUENCE: 25
gatctcgact ataaagaggg caggctgtcc tctaagcgtc accacgactt ca           52

<210> SEQ ID NO 26
```

```
<211> LENGTH: 52
<212> TYPE: DNA
<213> ORGANISM: mouse
<220> FEATURE:
<223> OTHER INFORMATION: The sequence is derived from a nucleotide
      sequence near the TATA box of a mouse metallothionein I
      gene. The sequence is introduced into human cells.

<400> SEQUENCE: 26
agcttgaagt cgtggtgacg cttagaggac agcctgccct ctttatagtc ga            52

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 27
tggaattgaa gtgaatggaa cagaagccaa gcaaggt                             37

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 28
tggccgcctg aggctttaga cttcctgatc ctcaa                               35

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 29
cccagccacc atgaacaga agccaagcaa ggtggagtgt                           40

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 30
tggccgcctg aggctttaga cttcctgatc ctcaa                               35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 31
ttactaacct ataacccca acagtatgac agaaa                                35

<210> SEQ ID NO 32
```

-continued

```
<211> LENGTH: 35
<212> TYPE: DNA
<213> ORGANISM: Artificial Sequence
<220> FEATURE:
<223> OTHER INFORMATION: Description of Artificial Sequence:primer for
      PCR with human cDNA

<400> SEQUENCE: 32
cagtctaatc ctcgaacact tccaggaaca aaggg                              35

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 33
cccagccacc atgacagaaa atggccttac agcttgggac                         40

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence:primer for
      adding Kozak consensus sequence to human cDNA

<400> SEQUENCE: 34
cagtctaatc ctcgaacact tccaggaaca aaggg                              35
```

CELL FOR MEASURING THE ABILITY TO CONTROL THE ACTIVITY OF A LIGAND-RESPONSIVE TRANSCRIPTION CONTROL FACTOR

BACKGROUND OF THE INVENTION

1. Field of the Invention

The present invention relates to a cell for measuring the ability of a chemical substance to control the activity of a ligand-responsive transcription control factor.

2. Description of the Related Art

A ligand-responsive transcription control factor is a protein functioning to promote transcription of a target gene on a DNA, such as a chromosome, in which said protein binds to a respective ligand to be activated and binds to a ligand-responsive transcription control factor recognizing sequence present in a transcription control region of said target gene. As such, the ligand-responsive transcription control factor plays important roles in maintaining homeostasis, reproduction, development and growth, cell differentiation, energy metabolism, drug metabolism and the like of organisms. It is known that when the transcription control by such a ligand-responsive transcription control factor is not normal, an abnormality occurs in the transcription activity of the target gene of said factor, causing various diseases and abnormalities.

In order to develop drugs useful for preventing and treating such diseases and abnormalities, there have been attempts searching for chemical substances having an activity to change the transcription control ability of a ligand-responsive transcription control factor. Further, there has been desired the development of efficient methods to investigate the activity of chemical substances over the transcription control ability of said ligand-responsive transcription control factor.

Nonetheless, it has been recently reported that some chemical substances in the environment show the action of a chemical substance in connection with the transcription control ability of a ligand-responsive transcription control factor, such as an allylhydrocarbon-like action or anti-allylhydrocarbon-like action, intranuclear hormone-like action or anti-intranuclear hormone-like action, estrogen-like action or anti-estrogen-like action, androgen-like action or anti-androgen-like action, thyroid hormone-like action or anti-thyroid hormone-like action, and the like (hereinafter, referred to as the present ligand-responsive transcription control action). Since there is a fear that such actions of chemical substances collapse the hormone balance in animals, disorder an ecosystem or cause diseases, there are attempts to measure the present ligand-responsive transcription control action of a chemical substance as a part in safety evaluations of a chemical substance.

In the case of estrogen for example, the action mechanism thereof may be as follows: when estrogen binds to an estrogen receptor present in the target cell of estrogen, such a receptor is activated, binds to an estrogen receptor-recognizing sequence present in a transcription control region of the target gene on the DNA, such as a chromosome, and promotes the transcription of the target gene. In this regard, there has been desired the development of test systems which can measure the ability of a chemical substance to control the estrogen receptor activity, as a method to measure the estrogen-like action or anti-estrogen-like action of a chemical substance.

Further, in the case of androgen for example, the action mechanism thereof may be as follows: when androgen binds to an androgen receptor present in the target cell of androgen, such an receptor is activated, binds to an androgen receptor-recognizing sequence present in a transcription control region of the target gene on a DNA, such as a chromosome, and promotes the transcription of the target gene. In this regard, there has been desired the development of test systems which can measure the ability of a chemical substance to control the androgen receptor activity, as a method to measure the androgen-like action or anti-androgen-like action of a chemical substance.

Furthermore, in the case of thyroid hormone for example, the action mechanism thereof may be as follows: when thyroid hormone binds to an thyroid hormone receptor present in the target cell of thyroid hormone, this receptor is activated, binds to a thyroid hormone receptor-recognizing sequence present in a transcription control region of the target gene on a DNA, such as a chromosome and promotes the transcription of the target gene. In this regard, there has been desired development of test systems which can measure the ability of a chemical substance to control the thyroid hormone receptor activity, as a method to measure the thyroid hormone-like action or anti-thyroid hormone-like action of a chemical substance.

SUMMARY OF THE INVENTION

The present inventors have intensively studied under such conditions and have resultantly succeeded in obtaining a cryopreservable cell which can be used to measure the action of a chemical substance over the transcription control ability of a ligand-responsive transcription control factor, thereby reaching the present invention.

The present invention provides:

1) an animal cell expressing a gene coding a ligand-responsive transcription control factor and securely maintaining a DNA comprising in a molecule, the following genes (a) and (b):

(a) a reporter gene connected downstream from a transcription control region, in which said transcription control region substantially consists of a recognition sequence of said ligand-responsive transcription control factor and a minimum promoter which can function in said cell; and (b) a selective marker gene which can function in said cell; provided that the following gene (c):

(c) a reporter gene connected downstream from a promoter which transcription activity is unchanged by having said responsive transcription control factor contacted with a ligand of said ligand-responsive transcription control factor, said reporter gene (c) coding a protein which can be differentiated from the protein coded by said gene (a)

is not present in said cell;

2) the cell according to the above 1, wherein said minimum promoter substantially consists of a TATA box;

3) the cell according to the above 1, wherein said ligand-responsive transcription control factor is one selected from an aryl hydrocarbon receptor, intranuclear hormone receptor, estrogen receptor, androgen receptor and thyroid hormone receptor;

4) the cell according to the above 1, wherein said ligand-responsive transcription control factor is an aryl hydrocarbon receptor;

5) the cell according to the above 1, wherein said ligand-responsive transcription control factor is an intranuclear hormone receptor;

6) the cell according to the above 1, wherein said ligand-responsive transcription control factor is an estrogen receptor;

7) the cell according to the above 1, wherein said ligand-responsive transcription control factor is an androgen receptor;

8) the cell according to the above 1, wherein said ligand-responsive transcription control factor is a thyroid hormone receptor;

9) an animal cell expressing an aryl hydrocarbon receptor and an Arnt receptor, and securely maintaining a DNA comprising in a molecule, the following genes (a) and (b):
   (a) a reporter gene connected downstream from a transcription control region, wherein said transcription control region substantially consists of a recognition sequence of said aryl hydrocarbon receptor and a minimum promoter which can function in said cell and
   (b) a selective marker gene which can function in said cell; provided that the following gene (c):
   (c) a reporter gene connected downstream from a promoter which transcription activity is unchanged by having said responsive transcription control factor contacted with a ligand of said ligand-responsive transcription control factor, said reporter gene (c) coding a protein which can be differentiated from the protein coded by said gene (a)

is not present in said cell;

10) use of an animal cell according to any one of the above 1 to 9 for evaluating an agonist activity or antagonist activity of a chemical substance over the transcription promoting ability of a ligand-responsive transcription control factor, in a reporter assay measuring the amount of a reporter gene under transcription control of said ligand-responsive transcription control factor;

11) a method for evaluating a chemical substance to have agonist activity over the transcription promoting ability of a ligand-responsive transcription control factor, said method comprising:
   (i) culturing an animal cell according to any one of above 1 to 9 in the presence of the chemical substance;
   (ii) measuring the expression amount of a reporter gene in said cell and
   (iii) assessing said chemical substance to have agonist activity over the transcription promoting ability of the ligand-responsive transcription control factor when the measured value of expression amount of said reporter gene introduced into said cell is larger than a measured value of expression amount of said reporter gene in the absence of said chemical substance;

12) a method for evaluating a chemical substance to have antagonist activity over the transcription promoting ability of a ligand-responsive transcription control factor, said method comprising:
   (i) culturing an animal cell according to any one of above 1 to 9 in the presence of the chemical substance and a ligand of said ligand-responsive transcription control factor;
   (ii) measuring the expression amount of a reporter gene in said cell and
   (iii) assessing said chemical substance to have antagonist activity over the transcription promoting ability of the ligand-responsive transcription control factor when the measured value of expression amount of said reporter gene introduced into said cell is smaller than a measured value of expression amount of said reporter gene in the presence of said ligand and the absence of said chemical substance;

13) a measuring kit comprising an animal cell according to any one of the above 1 to 9;

14) a method for obtaining an animal cell for measuring the ability to control the activity of a ligand-responsive transcription control factor, said method comprising:
   (i) introducing into an animal cell, a DNA comprising in a molecule the following genes (a) and (b):
      (a) a reporter gene connected downstream from a transcription control region, wherein said transcription control region substantially consists of a recognition sequence of said ligand-responsive transcription control factor and a minimum promoter which can function in said cell, and
      (b) a selective marker gene which can function in said cell, said animal cell being
         an animal cell that comprises a DNA comprising a gene coding the ligand-responsive transcription control factor introduced thereto before, after or during the same time of above step (i) or that naturally having an ability to express the gene coding the ligand-responsive transcription control factor, provided that a reporter gene (c) connected downstream from a promoter which transcription activity is unchanged by having said responsive transcription control factor contacted with a ligand of said ligand-responsive transcription control factor, said reporter gene (c) coding a protein which can be differentiated from the protein coded by said gene (a), is not present in the cell; and
   (ii) recovering from the transformed cell obtained from step (i), a transformed cell having said introduced DNA securely maintained therein;

15) the method according to the above 14, wherein said cell is an animal cell that comprises a DNA comprising a gene coding the ligand-responsive transcription control factor introduced thereto before, after or during the same time of the step (i);

16) the method according to the above 15, wherein the DNA comprising a gene coding the ligand-responsive transcription control factor, comprises in a molecule, a selective marker gene which can function in said cell and which codes a phenotype different from that of the gene (b).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE PREFERRED EMBODIMENTS

Figure 1:
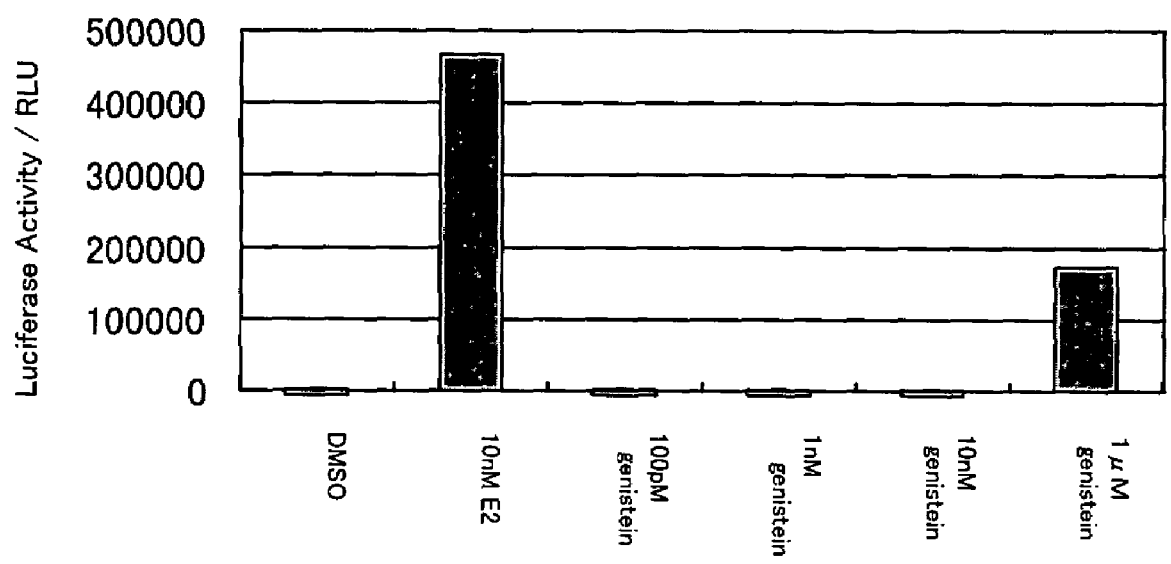
FIG. 1 is a view showing the results of a measurement of the ability of genistein to activate estrogen receptor α, by a reporter assay using a cell of the present invention for measuring the transcription activity of a gene receiving the transcription control of estrogen receptor α. Columns show, from the left side, an area in which only DMSO, which is used as a solvent for the chemical substance, is added (DMSO), an area in which 17β estradiol is added to a final concentration of 10 nM (10 nM E2), an area in which genistein was added to a final concentration of 100 pM (100 pM genistein), an area in which genistein is added to a final concentration of 1 mM (1 nM genistein), an area in which genistein is added to a final concentration of 10 nM (10 nM genistein), and an area in which genistein is added to a final concentration of 1 μM (1 μM genistein).
Figure 2:
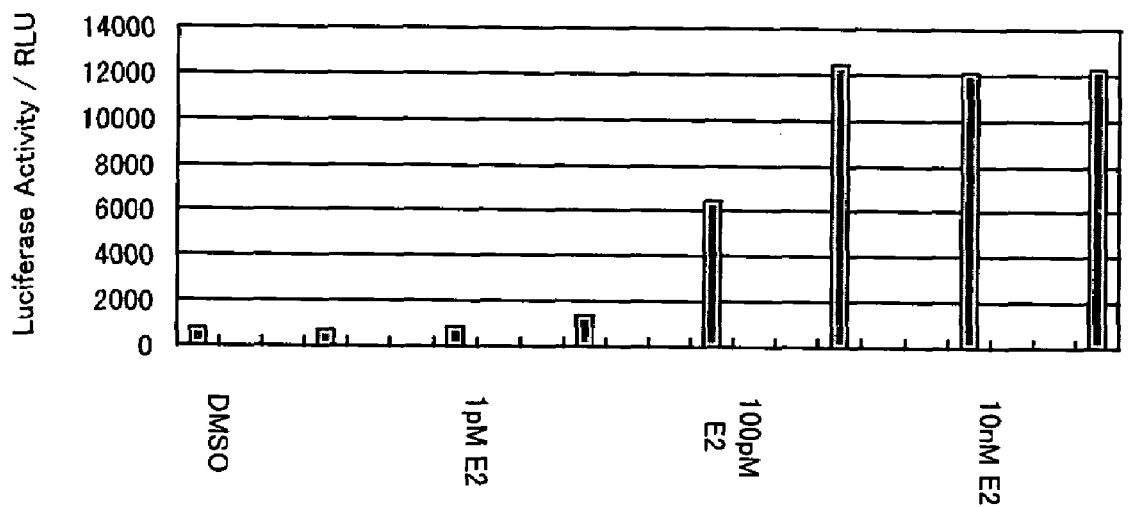
FIG. 2 is a view showing the results of a measurement of the ability of 17β estradiol to activate estrogen receptor α, by a reporter assay using a cell of the present invention. Columns show, from left side, an area in which only DMSO, which was used as a solvent for 17β estradiol, is added (DMSO), an area in which 17β estradiol is added to a final concentration of 0.1 pM, an area in which 17β estradiol is added to a final concentration of 1 pM (1 pM E2), an area in which 17β estradiol is added to a final concentration of 10 pM, an area in which 17β estradiol is added to a final concentration of 100 pM (100 pM genistein), an area in which 17β estradiol is added to a final concentration of 1 nM, an area in which 17β estradiol is added to a final concentration of 10 mM (10 nM E2), and an area in which 17β estradiol is added to a final concentration of 100 nM.
Figure 3:
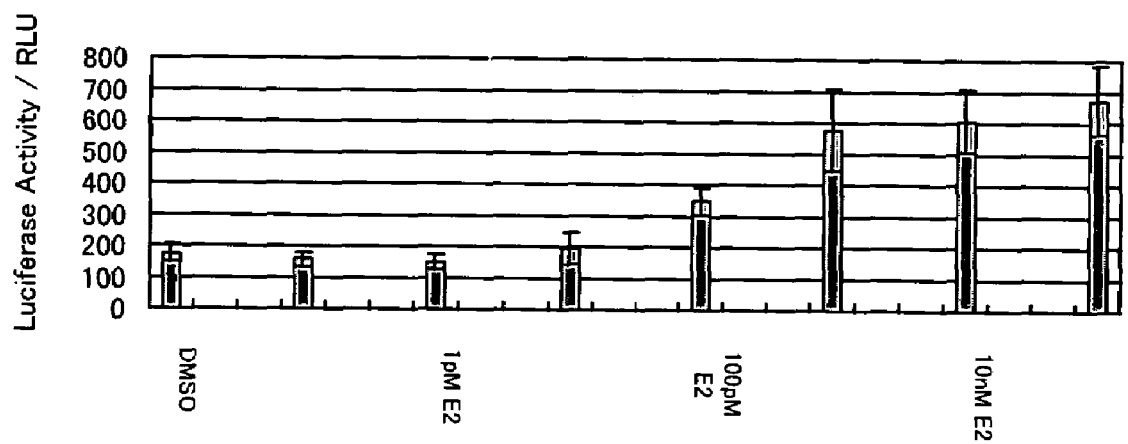
FIG. 3 is a view showing the results of a measurement of the ability of 17β estradiol to activate estrogen receptor β, by a reporter assay using a cell of the present invention. Columns show, from left side, an area in which only DMSO, which was used as a solvent for 17β estradiol, is added (DMSO), an area in which 17β estradiol is added to a final concentration of 0.1 pM, an area in which 17β estradiol is added to a final concentration of 1 pM (1 pM E2), an area in which 17β estradiol is added to a final concentration of 10 pM, an area in which 17β estradiol is added to a final concentration of 100 pM (100 pM E2), an area in which 17β estradiol is added to a final concentration of 1 nM, an area in which 17β estradiol is added to a final concentration of 10 nM (10 nM E2), and an area in which 17β estradiol is added to a final concentration of 100 nM.

The present invention will be described in detail below.

In the present invention, a ligand-responsive transcription control factor means a protein functioning to promote the transcription of the aforementioned target gene on a DNA, in which said protein binds to a ligand-responsive transcription control factor-recognizing sequence present in a transcription control region in a target gene on a DNA, with specific examples thereof including proteins called intranuclear hormone receptors of steroid hormones such as estrogen, androgen, glucocorticoid and the like, thyroid hormones, fat-soluble vitamins such as vitamin $D_3$, retinoin and the like, or prostinoid and the like receptors of insect hormone such as egdyson receptor and the like, allylhydrocarbon receptor which is a receptor of dioxin, and the like.

For example, the cell of the present invention may be prepared by recovering a cell expressing a gene coding the ligand-responsive transcription control factor and securely maintaining an introduced DNA comprising in a molecule both genes (a) a ligand-responsive reporter gene and (b) a selective maker gene which can function in the cell, provided that there is not present in the cell, (c) a reporter gene that is connected downstream from a promoter which transcription activity is unchanged by having said responsive transcription control factor contacted with a ligand of said ligand-responsive transcription control factor and which codes a protein that can be differentiated from the protein coded by said reporter gene.

As used herein, the phrase, a cell "securely maintaining" means that an introduced DNA does not fall out from a cell in some days, for example, about 5 to 7 days. Specifically, there can be mentioned, a condition in which the said introduced DNA is inserted into a chromosome.

Examples of cells which may be used in preparing the cell of the present invention include animal cells such as cells derived from a mammalian animal such as a human, mouse, rat and the like, cells derived from an insect and the like. In view of handling and reproducibility, cells which can produce stable passage are preferable. More specific examples thereof include a human-derived HeLa cell, human-derived MCF7 cell, human-derived HepG2 cell, mouse-derived NIH3T3 cell, mouse-derived Hepalclc7 cell, rat-derived H4IIE cell [all available from American Type Culture Collection (ATCC)] and the like.

Into a cell not producing the intended ligand-responsive transcription control factor, a gene coding the intended ligand-responsive transcription control factor is introduced in order to provide an expressible form thereof. Such a gene coding a ligand-responsive transcription control factor may be a naturally-occurring gene or a gene which has been modified artificially, such as a gene coding a protein to which a functional domain of a different transcription control factor is connected. This gene may also be a gene in which a consensus sequence of Kozak (Nucleic Acids Res., 12, 857-872 (1984)) is connected upstream from a translation initiation codon ATG thereof. The DNA of a gene of such a ligand-responsive transcription control factor may be prepared, for example, by designing and producing an oligonucleotide for amplifying a DNA coding such a factor, based on known nucleotide sequences, and by conducting a polymerase chain reaction (hereinafter, abbreviated as PCR) in which the produced oligonucleotide is used as a primer. Then, a heat-resistant polymerase prepared for Long-PCR method, for example, LA-Taq (manufactured by Takara Shuzo Co., Ltd.) and the like, may advantageously be used in PCR. For the template DNA used in PCR, for example, a reverse transcriptase is reacted with a commercially available mRNA derived from various cells, by using oligo dT as a primer to synthesize a DNA which can be used as the template. Alternatively, commercially available cDNA derived from various creatures may also be used.

Further, when using as the host cell, a cell producing the intended ligand-responsive transcription control factor, a gene coding the aforementioned ligand-responsive transcription control factor may be introduced into the cell for expression in a similar manner as described above, to reinforce the productivity of the aforementioned ligand-responsive transcription control factor. Alternatively, a gene coding a protein having a function to reinforce the transcription activity of a gene which receives transcription control from the aforementioned receptor such as a coactivator and the like of an intranuclear hormone receptor for example may also be introduced into the host cell for expression, so that the transcription control ability of an endogenous ligand-responsive transcription control factor may be reinforced.

Specifically, when the intended ligand-responsive transcription control factor is an allylhydrocarbon receptor, for example, as the cell which may be used for preparing the cell of the present invention, there may be exemplified animal cells such as cells derived from mammalian animals, cells derived from insects and the like which express both an allylhydrocarbon receptor gene, preferably the aforementioned gene and Arnt [Ah, receptor nuclear translocator, Science, 252, 954 to 958 (1991)] gene. More specifically, allylhydrocarbon receptor gene endogenous cells such as a mouse-derived Hepalclc7 cell, rat-derived H4IIE cell, human-derived HepG2 cell and the like are listed. Further, regarding allylhydrocarbon receptor gene non-endogenous cells such as a CV-1 cell and the like or cells in which the expression amount of the allylhydrocarbon receptor gene is small, it may be advantageous to have an allylhydrocarbon receptor gene introduced into the aforementioned cell as described above to increase the expression amount of the gene before use. As the allylhydrocarbon receptor gene to be introduced into a cell, a human-derived allylhydrocarbon receptor gene [GenBank Accession No. L19872, Mol. Pharmacol. 44, 911 to 917 (1993)], mouse-derived allylhydrocarbon receptor gene [GenBank Accession No. M94623, Proc. Natl. Acad. Sci. USA, 89, 8185-8189 (1992)], rat-derived allylhydrocarbon receptor gene [GenBank Accession No. M94623, Nucleic Acids Res., 22, 3038-3044 (1994)] and the like are listed.

A DNA containing a ligand-responsive reporter gene may be prepared, for example, by connecting upstream from the DNA of a reporter gene, a DNA having a transcription control region substantially consisting of a recognition sequence of the intended ligand-responsive transcription control factor and of a minimum promoter which can function in the cell.

In the present invention, there typically is securely introduced to a host cell with high frequency, a DNA comprising in a molecule, (a) a reporter gene connected downstream from a transcription control region, in which said transcription control region substantially consists of a recognition sequence of said ligand-responsive transcription control factor and a minimum promoter which can function in said cell and (b) a selective marker gene which can function in said cell. Further, there typically is securely introduced with high frequency to a stable transformed cell which is selected from such host cells above, a ligand-responsive reporter gene, depending on the characteristic of the selective marker.

A "recognition sequence of a ligand-responsive transcription control factor" is a specific nucleotide sequence present in the transcription control region of a target gene which the expression amount is controlled by a ligand-responsive transcription control factor, and when a complex of a ligand and a ligand-responsive transcription control factor recognizes this sequence and binds thereto, the transcription of a target gene present in the downstream therefrom is promoted. Usually, this sequence may also be sometimes classified, based on the kind of corresponding ligand and be called a glucocorticoid-responsive sequence (GRE: glucocorticoid responsive element, Nature., 318, 635-641 (1985)), PPRE (Peroxisome Proliferator responsive element, J. Steroid Biochem., Mol. Biol., 51, 157-166 (1994)), estrogen-responsive sequence (ERE; estrogen responsive element), androgen-responsive sequence (ARE; androgen responsive element), thyroid hormone-responsive sequence (TRE; thyroid hormone responsive element), dioxin-responsive sequence (DRE; dioxin-responsive element, J. Biol. Chem., 263, 17221-17224 (1988)), xenobiotic-responsive element (XRE) and the like, respectively. Specific examples of the recognition sequence of an allylhydrocarbon receptor, which is a dioxin-responsive sequence, include nucleotide sequences on 5' upstream region of genes derived from mammalian animals such as cytochrome P4501A1 gene [cyp1A1, J, Biol. Chem., 263, 17221-17224 (1988), Nucleic Acids Res., 15, 4179-4191 (1987)], glutathione S-transferase Ya subunit gene [Proc. Natl. Acad. Sci. USA, 87, 3826-3830 (1990)], UDP-glucuronyl transferase gene [J. Biol. Chem., 271, 3952-3958 (1996)] and the like. There may also be listed nucleotide sequences containing one or more of a consensus sequence [core sequence: 5'-(T/A)GCGTG, J. Biol. Chem., 271, 3952-3958 (1996)] of a dioxin-responsive sequence. As the recognition sequence of an estrogen receptor which is an estrogen-responsive sequence, there may be listed nucleotide sequences on the 5' upstream sequence of a vitellogenin gene of *Xenopus* (Cell., 57, 1139-1146) and the like, for example. There may also be listed nucleotide sequences containing one or more of a consensus sequence [5'-AGGTCAnnnTGACCTT-3'] of an estrogen-responsive sequence. Specific examples of the recognition sequence of an androgen receptor include the nucleotide sequences in LTR of mouse papilloma virus (MMTV) (Nucleic Acids Research., 19, 1563-1569), and the like, and specific examples of the recognition sequence of a thyroid hormone receptor include nucleotide sequences given in Glass, C. K., et al., Endocrine Rev., 15, 391-407 (1994) and the like. For obtaining sufficient transcription control ability, it is preferable that the consensus sequence as described above is usually connected about 2 to 5 tandem. DNA having such nucleotide sequences may be prepared by chemical synthesis, or by amplifying and cloning by PCR methods and the like.

The "minimum promoter" is a DNA having a region which determines the transcription initiation site by RNA polymerase II and relates to maintaining a minimum transcription level, and is also called a core promoter. Usually, the minimum promoter is also a region which is found in a relatively narrow portion near the transcription initiation site of a gene. As the nucleotide sequence in such a region, there are listed, for example, a TATA box and nucleotide sequences near the transcription initiation point, preferably is a short nucleotide sequence of about 40 to 100 bp. and more preferably about 50 bp. Specific examples thereof include nucleotide sequences (Genbank Accession No. J00605) from −33 base (Transcription initiation point is +1. Hereinafter, the same.) to +15 base in the 5' upstream region of metallothionein I gene of mouse, nucleotide sequences (Genbank Accession No. J00895) from −40 base to +10 base in the 5' upstream region of chicken ovalbumin gene and the like.

The transcription activity of the "minimum promoter" used in the cell of the present invention is preferably weaker than the transcription activity of a DNA region containing, for example, nucleotide sequences from −130 base to +53 base in the 5' upstream region of thymidinekinase (tk) derived from herpes simplex virus (HSV) (Proc. Natl. Acad. Sci. USA, 78, 1411-1445 (1981), since in this case, the constitutive background transcription activity in measuring transcription activity lowers and the detection of ligand-responsive transcription activity can be conducted with higher sensitivity. DNA containing the nucleotide sequence as described above may be prepared, for example, by chemical synthesis based on the nucleotide sequence thereof. Alternatively, this DNA may be prepared by, for example, designing and producing an oligonucleotide for amplifying DNA coding the region as described above, based on known nucleotide sequences, and conducting PCR using the produced oligonucleotide as a primer.

The phrase that "transcription control region substantially consists of a recognition sequence of said ligand-responsive transcription control factor and of a minimum promoter which can function in said cell" means a transcription control region containing exclusively the intended ligand-responsive transcription control factor recognition sequence and minimum promoter, as the main functional element relating to transcription control, and for example, can mean a sequence which does not contain other functional elements relating to the transcription control of a recognition sequence of the other transcription control factor and the like, or even if it does contain such a functional element, a sequence which does not have the transcription control ability substantially changed by the above-mentioned ligand-responsive transcription control factor recognition sequence and minimum promoter.

Further, the above-mentioned phrase a "reporter gene connected downstream from a transcription control region" means a reporter gene connected to a transcription control region so that said reporter gene is expressed under control of the transcription control region in a host cell into which the gene is introduced.

As a "reporter gene" which is an indicator of transcription activity, a gene which expression amount can be measured based on the enzyme activity and the like of the transcription product thereof (reporter protein) is preferable because the measurement of the expression amount of the gene is easy, with examples thereof including genes coding enzyme proteins such as fire fly luciferase, Renilla luciferase, β-galactosidase, chloramphenicolacetyltransferase, alkaliphosphatase and the like. DNA of such a reporter gene may be obtained, for example, by using a restriction enzyme to digest a DNA of commercially available plasmids containing such reporter genes and isolating the intended DNA, as well as by other like procedures.

The DNA used for the transformation of a host cell in producing the cell of the present invention includes, in addition to the above-mentioned reporter genes, selective marker genes which can function in the host animal cell. The "selective marker gene" is a gene coding a phenotype which can be a mark in differentiating a cell which has been transformed by DNA containing the gene from a non-transformed cell. The phrase "which can function in a cell" means that the above-mentioned phenotype can be expressed in the cell, and for example, there are mentioned genes which can be expressed in the cell under control of a promoter having a transcription initiation ability in the cell and which codes the phenotype for selecting cells effective in said cell. As a cell selective marker gene effective in a cell, there are for example listed genes which can provide the cell with a resistance against chemicals suppressing or disturbing proliferation of the cell, with specific examples thereof including neomycin-resistant genes (aminoglycosidephosphotransferase gene), hygromycin-resistant genes (hygromycinphosphotransferase gene), blastcidin S-resistant genes (blastcidin S deaminase gene) and the like. The blastcidin S-resistant genes are preferably mentioned since selection of transformed cells can be conducted in a shorter period of time. The blastcidin S-resistant gene can be obtained, for example, from commercially available plasmid pUCSV-BSD and the like.

The "DNA comprising in a molecule the following genes (a) and (b): (a) a reporter gene connected downstream from a transcription control region in which said transcription control region substantially consists of a recognition sequence of a ligand-responsive transcription control factor and of a minimum promoter which can function in the cell and (b) a selective marker gene which can function in the cell" may be prepared, for example, by integrating these genes into the same vector. As the vector, there is mentioned plasmids, viral vectors, episomes and the like. Preferably, the vector is easy to use and may have a compact size since it is desired to have a low frequency of falling out from stable cell transformation or from genetic recombination between vectors or within a vector. For example, plasmids of about 2 kb to 10 kb are listed. Further, since the operation of integrating genes into the vector can be conducted efficiently when E. coli is used as a host, the vector preferably has an additional function as a E. coli vector, namely, having a replication origin, a chemical-resistant gene, a restriction enzyme recognition site for gene insertion, and the like which can function in E. coli. More specifically, DNA having the above-mentioned constitution may be prepared, for example, as follows: a DNA comprising a nucleotide sequence which is derived from the 5' upstream region of a vitellogenin gene of Xenopus, in which there is contained an estrogen receptor recognition sequence and a minimum promoter derived from mouse metallothionein I gene, are integrated into the upstream of fire fly luciferase gene (reporter gene) kept in a plasmid. Further, a blastcidin S-resistant gene connected to a SV 40 early promoter, for example, can be integrated into the above-mentioned plasmid. Then, the thus prepared DNA is introduced into host cells by a conventional genetic engineering procedure to give transformed cells from which stable transformed cells in which this DNA is securely maintained in the cell are obtained.

Further, when the intended ligand-responsive transcription control factor is an estrogen receptor, there are listed, as the cell which can be used for preparing the cell of the present invention, animal cells, such as mammalian animal-derived cells and the like, which express an estrogen receptor gene. For expression of an estrogen receptor gene in a host cell, it may be advantageous that this gene is inserted into a vector so that this is connected functionally downstream of a promoter which can function in a cell, and be introduced into the host cell. The phrase "connected functionally downstream from a promoter" means a configuration which has the promoter bound to cause expression in the host cell. Examples of the promoter which can function in animal cells include Rous sarcoma virus (RSV) promoter, cytomegalovirus (CMV) promoter, simian virus (SV40) early or late promoter, mouse mamilla tumor virus (MMTV) promoter and the like. As the vector, plasmids containing a replication origin and a chemical-resistant gene for E. coli, and the like are listed, and commercially available vectors for expression having a promoter as described above and having a gene insertion site downstream therefrom may be used. If the DNA of a vector which has had inserted an estrogen receptor gene functionally connected downstream from a promoter which can function in animal cells, is introduced into the host cell to obtain stable transformed cells in which the gene is securely maintained therein, then time for conducting gene introduction transiently at every test can be saved. The DNA containing such an estrogen receptor gene may be introduced into a host cell together with the DNA containing in a molecule both of a ligand-responsive reporter gene and a selective marker gene, or may be introduced sequentially separate. In the DNA containing such an estrogen receptor gene, when a selective marker gene which can function in a host cell and which codes a phenotype different from that of a selective marker gene contained in the DNA used for introducing a reporter gene described below is contained in the same molecule, selection of transformed cells is easier.

Examples of the estrogen receptor gene introduced into the host cell include EDNA genes derived from a human estrogen receptor a gene (GenBank Accession No. X03635), human estrogen receptor β gene (Biochem. Biophysical. Research. Com., 243, 122-126 (1998)), rat estrogen receptor α gene (GenBank Accession No. X61098), rat estrogen receptor β gene (GenBank Accession No. U57439), mouse estrogen receptor a gene (GenBank Accession No. M38651) and the like. These genes may also be genes in which a consensus sequence of Kozak (Nucleic Acids Res., 12, 857-872 (1984)) is connected upstream from a translation initiation codon ATG thereof.

When the intended ligand-responsive transcription control factor is an androgen receptor, there are listed, as the cell which may be used for preparing the cell of the present invention, animal cells such as mammalian animal-derived cells and the like which express an androgen receptor gene. For expression of an androgen receptor gene in a host cell, it may be advantageous that this gene is inserted into a vector so that this gene is connected functionally downstream from a promoter which can function in a cell and be introduced into the host cell. The phrase "connected functionally downstream from a promoter" means a configuration which has the promoter bound to cause expression in the host cell. Examples of the promoter which can function in animal cells include Rous sarcoma virus (RSV) promoter, cytomegalovirus (CMV) promoter, simian virus (SV40) early or late promoter, mouse mamilla tumor virus (MMTV) promoter and the like. As the vector, plasmids containing a replication origin and chemical-resistant gene for E. coli, and the like are listed, and commercially available vectors for expression having a promoter as described above and having a gene insertion site downstream therefrom may also be used. If the DNA of a vector into which has had inserted an androgen receptor gene functionally connected downstream from a promoter which can function in animal cells, is introduced into host cells to obtain stable transformed cells in which the gene is securely maintained therein, then time for conducting gene introduction transiently at every test can be saved. The DNA containing such an androgen receptor gene may be introduced into a host cell together with the DNA containing in a molecule both of a ligand-responsive reporter gene and a selective marker gene, or may be introduced sequentially separate. In the DNA containing such an androgen receptor gene, when a selective marker gene which can function in a host cell and which codes a phenotype different from that of a selective marker gene contained in the DNA used for introducing a reporter gene described below is contained in the same molecule, selection of transformed cells is easier.

Examples of the androgen receptor gene introduced into the host cell include cDNA genes derived from a human androgen receptor α gene (GenBank Accession No. M23263), rat androgen receptor gene (GenBank Accession No. M23264), mouse androgen receptor gene (GenBank Accession No. X59592) and the like. These genes may also be genes in which a consensus sequence of Kozak (Nucleic Acids Res., 12, 857-872 (1984)) is connected at the upstream of a translation initiation codon ATG thereof.

When the intended ligand-responsive transcription control factor is a thyroid hormone receptor, there are listed, as the cell which may be used for preparing the cell of the present invention, animal cells such as mammalian animal-derived cells and the like which express a thyroid hormone receptor gene. For expression of a thyroid hormone receptor gene in a host cell, it may be advantageous that this gene is inserted into a vector so that this gene is connected functionally downstream from a promoter which can function in a cell and be introduced into the host cell. The phrase "connected functionally downstream from a promoter" means a configuration which has the promoter bound to cause expression in the host cell. Examples of the promoter which can function in animal cells include Rous sarcoma virus (RSV) promoter, cytomegalovirus (CMV) promoter, simian virus (SV40) early or late promoter, mouse mamilla tumor virus (MMTV) promoter and the like. As the vector, plasmids containing a replication origin and chemical-resistant gene for E. coli, and the like are listed, and commercially available vectors for expression having a promoter as described above and having a gene insertion site downstream therefrom may also be used. If DNA of a vector into which has had inserted a thyroid hormone receptor gene functionally connected downstream from a promoter which can function in animal cells, is introduced into host cells to obtain stable transformed cells in which that gene is securely maintained therein, then time for conducting gene introduction transiently at every test can be saved. The DNA containing such a thyroid hormone receptor gene may be introduced into a host cell together with the DNA containing in a molecule both of a ligand-responsive reporter gene and a selective marker gene, or may be introduced sequentially separate. In DNA containing such a thyroid hormone receptor gene, when a selective marker gene which can function in a host cell and which codes a phenotype different from that of a selective marker gene contained in the DNA used for introducing a reporter gene described below is contained in the same molecule, selection of transformed cells is easier.

Examples of the thyroid hormone receptor gene introduced into a host cell include cDNA genes derived from a human thyroid hormone receptor α gene (GenBank Accession No. M24748), human thyroid hormone receptor β gene (GenBank Accession No. M26747), rat thyroid hormone receptor α gene (GenBank Accession No. M18028), rat thyroid hormone receptor β gene (GenBank Accession No. M03819) and the like. These genes may also be genes in which a consensus sequence of Kozak (Nucleic Acids Res., 12, 857-872 (1984)) is connected at the upstream of a translation initiation codon ATG thereof.

There is not present in the cell of the present invention, a DNA (hereinafter referred to as the cell number reporter gene) which is prepared by connecting the DNA of a reporter gene with the DNA of a promoter of which transcription activity is unchanged by having said responsive transcription control factor contacted with a ligand of the ligand-responsive transcription control factor, said reporter gene coding a protein that can be differentiated from the protein coded by the reporter gene connected downstream from a transcription control region, wherein said transcription control region substantially consists of the recognition sequence of the ligand-responsive transcription control factor and the minimum promoter which can function in said cell.

Such a cell is not usually obtained unless an artificial operation described below in which a cell number reporter gene is purposefully introduced is applied, and for example, the presence or absence of the cell number reporter gene can be confirmed by conventional genetic engineering procedures such as PCR, hybridization and the like. Further, if the enzyme activity or the like of the protein coded by the reporter gene contained in a cell number reporter gene is measured, then the cell can also be confirmed by the presence or absence of the enzyme activity thereof or the like.

However, when there is a need to know the number of cells by measuring protein amount from the cell for obtaining highly accurate measured values and the like, it may be advantageous, separately, to introduce a cell number reporter gene into the cell of the present invention and to use the resultant transformed cell.

As the reporter gene contained in a cell number reporter gene, a gene of which expression amount is easily measured by the enzyme activity of the protein coded by the gene is preferable and which is a different reporter gene coding a protein which can be differentiated from a protein coded by a reporter gene used in the above-mentioned ligand-responsive transcription control factor. The differentiation may be conducted, for example, by differences in enzyme activity, substrate specificity and the like. The DNA of such a reporter gene may be obtained, for example, by digesting, using a restriction enzyme, DNA of commercially available plasmids containing these reporter genes, and isolating the intended DNA, as well as by other like procedures.

The "promoter which transcription activity is unchanged by having said responsive transcription control factor contacted with a ligand of the ligand-responsive transcription control factor" is a promoter which is not controlled by the recognition sequence of the ligand-responsive transcription control factor as described above and has constitutive transcription ability, with examples thereof including a tk promoter, RSV promoter, CMV promoter and the like. The DNA of such a promoter may be obtained, for example, by digesting, using a restriction enzyme, DNA of commercially available plasmids containing these reporter genes, and isolating the intended DNA, as well as by other like procedures.

It is also possible to prepare a DNA containing a cell number reporter gene by inserting the DNA of the above-mentioned reporter gene downstream from such a promoter of commercially available plasmids containing the promoter.

The intended cell may be prepared by integrating the DNA containing the ligand-responsive reporter gene and the DNA containing the cell number reporter gene into vectors such as plasmids and the like, respectively, and introducing the vectors into the above-mentioned cell, by selecting cells in which these reporter genes are securely maintained therein. Specifically, when the intended ligand-responsive transcription control factor is an allylhydrocarbon receptor, a plasmid integrated with a fire fly luciferase (ligand-responsive transcription control factor) connected downstream from a nucleotide sequence containing a dioxin-responsive sequence derived from the 5' upstream region of cytochrome P4501A1 gene and downstream from a nucleotide sequence necessary for initiation of transcription derived from the 5' upstream region of a glutathione S-transferase Ya subunit gene, as well as a plasmid integrated with a *Renilla* luciferase gene (cell number reporter gene) connected downstream from a tk promoter, are prepared, and these plasmids are introduced into an allylhydrocarbon receptor gene-endogenous Hepalclc7 cell. In such cases, an expression plasmid of a selective marker gene such as a chemical-resistant gene and the like may also be introduced simultaneously, to provide easy selection of the cells into which these reporter genes have been introduced. Examples of the chemical-resistant gene which may be used as described above include a neomycin-resistant gene (aminoglycosidephosphotransferase), blastcidin S-resistant gene, hygromycin-resistant gene and the like.

To introduce the DNA of a plasmid integrated with the above-mentioned both reporter genes into, for example, cells derived from mammalian animals, first, for example, the cells are placed in a culturing vessel ($10^5$ to $10^7$ cells/dish of 6 to 10 cm diameter) and cultured for several hours to about overnight at 37° C. under the conditions of 5% $CO_2$ and saturated humidity using an αMEM medium containing about 5 to 10% (w/v) serum. Into the thus cultured cells, plasmid DNA integrated with reporter genes is introduced. As the method for introducing DNA into a cell, a conventional lipofection method, DEAE-dextran method, calcium phosphate method, electroporation method and the like are listed. Specifically, when a commercially available lipofectin (manufactured by GIBCO-BRL) is used, it is advantageous that an operation is conducted according to the appended manual, and that the amount of plasmid DNA introduced, the amount of a lipofectin, the kind of a cell, the number of cells and the like are previously investigated and the optimum conditions are determined. When a plasmid containing a chemical-resistant gene is introduced together with a plasmid integrated with a reporter gene, it may be advantageous that the amount of DNA of a plasmid containing a chemical-resistant gene is at about ⅕ to 1/10 of the amount of DNA of a plasmid integrated with a reporter gene. As the plasmid DNA, DNA purified by a CsCl density gradient centrifugal method or DNA having an equivalent purity is used, and it may also be possible to use a plasmid DNA linearized by previous digestion with a restriction enzyme having no recognition site in regions (a recognition sequence of ligand-responsive transcription control factor, promoter, reporter gene, selective marker gene and the like) necessary for the preparation of the cell of the present invention. After introduction of a plasmid DNA into the cell, the medium is substituted with a serum-containing medium, and the culturing is continued for about overnight to 2 days. Next, the cell is removed from the culturing vessel by trypsinization or the like according to a conventional method and transferred a new culturing vessel. Directly after being transferred, or after culturing for 1 to 2 days, the medium is substituted with a medium having conditions corresponding to a selective marker gene introduced into the cell, and the culturing is continued in the medium having conditions corresponding to a selective marker gene until non-transformed cells disappear and a colony derived from the transformed cell becomes an appropriate size. During this procedure, culture exchange is conducted at a rate of 1 to 2 times a week, if necessary. By conducting such procedures, the cell securely maintaining the reporter gene therein can be obtained so that the stable transformed cell can be recovered. If necessary, the above-described operation for introducing a reporter gene may be repeated. To confirm that the introduced reporter gene is securely maintained in the cell, it may be advantageous to prepare the DNA of this cell according to a conventional genetic engineering procedure, and to detect the presence of this reporter gene by utilizing a method such as PCR, southern hybridization method and the like using as a primer, a probe, a DNA fragment having a partial nucleotide sequence of the introduced reporter gene or the like.

Next, it is possible to select cells preferable for measuring agonist or antagonist activity of a chemical substance over transcription promotion ability of a ligand-responsive transcription control factor, by utilizing as an indicator, the ligand-responsiveness in the expression amount of the reporter gene in the thus obtained cell. Specifically, first, the thus obtained colony is divided into several portions and inoculated again, the cells are allowed to grow, a solution of a ligand of the intended ligand-responsive transcription control factor is then added to a portion of the grown cells (ligand addition district) and cultured for about 4 hours to 2 days, and the expression amounts of the ligand-responsive reporter gene and cell number reporter gene are then measured. Further, as controls, only the solvent used for the preparation of the above-mentioned ligand solution is added to another portion of the above-mentioned cells (control district) and cultured in a similar manner, such that the expression amounts of the respective reporter genes are measured.

Though the method for measuring the expression amount of a reporter gene depends also on the kind of a reporter gene used, in usual cases, a cell lysis agent is added to the target cell which is to be measured to prepare a cell extracted solution, and the amount of proteins which are coded by the reporter gene contained in the resultant extracted solution is measured. For example, when a protein coded by the reporter gene has enzyme activity, a substrate specific to this enzyme is allowed to react with the cell extracted solution containing proteins coded by the reporter gene and the amount of the remaining substrate and the amount of the reaction product are measured utilizing the light emission amount, fluorescent absorbance or absorbancy ot the likeas indicators. Specifically, in the case of use of a luciferase gene as the reporter gene, if luciferin, which is a substrate of luciferase, is reacted with a cell extracted solution, the light emission occurs at a strength in proportion to the amount of luciferase in the cell extracted solution. Therefore, by measuring this light emission strength by a measurement apparatus such as a luminometer and the like, the amount of luciferase in the cell extracted solution, and the expression amount of a luciferase gene may be determined.

Regarding the expression amounts of a reporter gene, by subtracting the expression amount in a control district from the expression amount in a ligand addition district, the increase in the expression amount of the reporter gene by contact with the ligand is determined. Then, cells may be selected in which the increase in the expression amount of a reporter gene by contact with the ligand is at least 2-fold, preferably 10-fold or more of the expression amount in a control district. Further, in the case wherein the cell of the present invention comprises the cell number reporter gene, since it is preferable that the expression amount of a cell number reporter gene does not vary by contact with a ligand, cells may be advantageously selected in which the increase in the expression amount of a cell number reporter gene by contact with the ligand is at least half or less of the increase in the expression amount of a ligand-responsive reporter gene by contact with the same ligand. Further, when there is not present in the thus obtained colony, an uniformly transformed cell, the cells are diluted and further cultured, and colonies having uniformly transformed cells are selected.

To prepare the cell of the present invention, it may be advantageous, that the "DNA comprising in a molecule the following genes (a) and (b): (a) a reporter gene connected at the downstream from a transcription control region in which said transcription control region substantially consists of a recognition sequence of said ligand-responsive transcription control factor and of a minimum promoter which can function in the cell, and (b) a selective marker gene which can function in said cell" prepared as described above is introduced into host cells, and stable transformed cells are recovered. Specifically, first, host cells such as a MCF7 cell and the like are transferred to a dish ($10^5$ to $10^7$ cells/dish of 6 to 10 cm diameter), and cultured for about several hours to overnight at 37° C. under conditions of 5% $CO_2$ and saturated humidity using an αMEM medium containing about 5 to 10% (v/v) serum. Into the thus cultured cells, the above-mentioned DNA is introduced. As the method for introducing DNA, conventional methods such as a conventional electroporation method, calcium phosphate method, lipofection method and the like are listed. Specifically, when a commercially available lipofectamine (manufactured by GIBCO) is used, it is advantageous that an operation is conducted according to the appended manual. And it is advantageous that the amount of lipofectamine based on the cell amount, the amount DNA introduced and the like are previously investigated and that the optimum conditions are determined. The purity of a DNA introduced into a host cell is desirably a purity of plasmid DNA purified by a CsCl density gradient centrifugal method or approximately an equivalent purity. Regarding the form of DNA introduced into a host cell, DNA of a plasmid integrated with the ligand-responsive reporter gene and selective marker gene as described above may also be introduced intact in the form of a ring into a host cell, however, in general cases, it may be advantageous that DNA linearized by cut at a restriction enzyme site present in a region exerting no effect on the expression of each gene that is introduced into a host cell.

To obtain a cell securely maintaining a DNA introduced, first, a cell into which the DNA has been introduced as described above is cultured without any additional treatment for about one day in a usual cell culturing solution (medium). Then, the cell is removed according to an ordinary method (trypsinization and the like), and transferred again, and then, directly, culturing is initiated under selective conditions corresponding to the cell selective marker gene introduced in a host cell. Namely, when the cell selective marker gene is a chemical-resistant gene, the chemical to which the transformed cell is resistant, is added to the medium, and the culturing is continued in the presence of the chemical until a colony derived from the transformed cell becomes an appropriate size, such as for 1 to 2 weeks. During this procedure, exchange with a new medium to which the chemical is added may be conducted at a rate of 1 to 3 times a week, if necessary. By recovering the thus obtained colony, a stable transformed cell is obtained.

After the recovered colony is divided into several portions and inoculated again, cells are allowed to grow, then, a solution containing a ligand of the intended ligand-responsive transcription control factor is added to a portion of the grown cells and cultured for about 24 hours, such that the expression amounts of the ligand-responsive reporter gene can be measured. Further, as controls, the expression amounts of systems in which only a solvent is added are measured. Though the method for measuring the expression amount of a ligand-responsive reporter gene used, in usual cases except cases in which a reporter gene product is secreted in a medium, the plasma membrane of the cell is broken by a cell lysis agent treatment, ultrasonic treatment and the like, to prepare a cell extracted solution and quantify the reporter gene product contained in this cell extracted solution. For example, when the reporter gene product is an enzyme protein, the enzyme protein in the extracted solution is reacted with a substrate specific to this enzyme, and the enzyme activity by the reporter gene product is quantified by measuring the light emission amount, fluorescent amount, absorbancy add the like, and is used as an indicator for the amount of the reporter gene product, and in extension, an indication for the expression amount of the reporter gene. Cells in which the expression amount of a reporter gene in the system in which a cell is allowed to contact a ligand is at least 2-fold, preferably 5-fold or more based on the expression amount of a reporter gene in the system in which only a solvent is added, are recovered. When there is not present in the thus obtained colony, uniformly transformed cells, the cells are diluted and further cultured, and colonies having uniformly transformed cells are selected.

The cell of the present invention obtained as described above can be utilized, for example, to identify a chemical substance showing agonist action and a chemical substance showing antagonist action against a ligand-responsive transcription control factor.

Specifically, first, the cells of the present invention are put into a cell culturing vessel and cultured. For example, when a 6-well plate is used, it may be advantageous that cells in a number of about $10^3$ to $2\times10^4$ per one well are placed therein, and cultured for about several hours to overnight. Further, when a medium to which serum has been added is used, it may also be permissible that the serum to be added to a medium is treated by for example activated carbon and the like to previously remove a ligand contained in the serum. Then, the chemical substance is added to this cell cultured solution. When the agonist activity of the chemical substance is measured, a solution having the chemical substance dissolved in the solvent or only the solvent is added to the above-mentioned cell culturing solution so that the final volumic concentration of the solvent in the culturing solution is from 0.5% to 2%. Further, when the antagonist activity of a chemical substance is measured, there are prepared a system obtained by adding a solution prepared by dissolving a ligand of the intended ligand-responsive transcription control factor (in the case of an allylhydrocarbon receptor, the ligand thereof, for example, dioxin, in the case of an estrogen receptor which is one of the intranuclear hormone receptor, the ligand thereof, for example, 17β-estradiol, in the case of an androgen receptor which is one of the intranuclear hormone receptors, the ligand thereof, for example, dihydrotestosterone (hereinafter, abbreviated as DHT), in the case of a thyroid hormone receptor which is one of the intranuclear hormone receptors, the ligand thereof, for example, 3,3',5-Triiodo-L-thyronine (3,5, 3')(hereinafter, abbreviated as T3), and the like) in a solvent to the above-mentioned culturing solution so that the concentration of the ligand in the culturing solution is usually near $EC_{50}$, and a system obtained by further adding a chemical substance to the above-mentioned system. The solvent to be added to the culturing solution as described above, for example, typically uses distilled water, dimethylsulfoxide (DMSO), ethanol and the like. When a chemical substance is added in the form of an aqueous solution, it may be advantageous that this aqueous solution is sterilized by filtration through a filter having a pore size of 20 μm or less, and the like, then, and then added to a culturing system.

After the above-mentioned cell is cultured, for example, for several hours to 72 hours, then, the expression amount of a reporter gene is measured as described above. For example, when the reporter gene is a fire fly luciferase gene, first, the culture supernatant is removed, the cells adhered to vessel walls are then washed with PBS (-) and the like, and a cell lysis agent and the like are added to the cells to break the cells to prepare a cell extracted product. This cell extracted product, as a sample of luciferase which is a reporter gene product therein, is reacted with luciferin which is a substrate of luciferase, and the obtained amount of light emission is quantified. In the test system for measuring the agonist activity of a chemical substance, when the luciferase activity per cell is higher in a cell of the system in which a chemical substance is added than in a cell of the system in which only a solvent is added, such as when the amount of a reporter gene product is larger, it is judged that this chemical substance shows agonist activity over the ligand-responsive transcription control factor. Further, in a test system for measuring the antagonist activity of a chemical substance, when the luciferase activity of a cell of the system in which the ligand and chemical substance are added is lower as compared with the luciferase activity of a cell of the system in which only a ligand of a ligand-responsive transcription control factor after the test is added, it is judged that the chemical substance has an antagonist activity on the ligand-responsive transcription control factor.

In the system for examination as described above, when a chemical substance shows non-specific toxicity in a cell, the transcription activity of a reporter gene may sometimes decrease irrespective of the transcription control ability of a ligand-responsive transcription control factor. Further, when a chemical substance shows non-specifically transcription promoting action or transcription suppressing action on a minimum promoter, the transcription activity of a reporter gene may sometimes increase or decrease irrespective of the transcription control ability of a ligand-responsive transcription control factor. Then, if necessary, it may also be permissible, for example, to prepare a cell which is stably transformed with a reporter gene functionally connected to a promoter having a function to constitutively transcribe a gene, and then have that used as a comparative control against the cell of the present invention. Specifically, for example, DNA containing a reporter gene connected functionally to a RSV promoter, TK promoter or the like is prepared, and host cells are then stably transformed with the DNA. Among the resulting colonies, cells expressing constitutively and stably a reporter gene (hereinafter, referred to as control cell) are selected. This cell is allowed to contact with a chemical substance in a similar manner as described above, and the expression amount of the reporter gene is quantified. When the expression amount of a reporter gene of the cell decreases or increases by contact of the chemical substance, it is indicated that this chemical substance shows non-specific action on a cell or promoter. Then, it may also be permissible that the results of a test using the cell of the present invention are appropriately corrected based on such results and the action of a chemical substance on a ligand-responsive transcription control factor as described above can be evaluated.

As described above, the transcription activity of a gene receiving the transcription control of a ligand-responsive transcription control factor using the cell of the present invention may be measured in the presence of various chemical substances, and the action of the chemical substance on the ligand-responsive transcription control factor may be evaluated based on this measurement, and an agonist and antagonist against the ligand-responsive transcription control factor may be identified. Such evaluation and identification methods may be utilized for detection of endocrine disruptors and the like having the present ligand-responsive transcription control action, and for a search of active ingredients of medicines targeting a ligand-responsive transcription control factor.

The cell of the present invention is cryopreservable, and can be activated for use if necessary. By use of the cell of the present invention, complicated operations such as introduction of a gene, selection of cells and the like in every test can be excluded as compared with the case of using a cell into which a ligand-responsive reporter gene has been transiently introduced. Further, cells having a specified ability can be used in the test, so that measurements with excellent reproducibility are possible.

Consequently, the cell of the present invention is also useful, for example, in conducting search, detection and the like of chemical substances as described above by an automated large scale screening method such as high through put screening and the like.

EXAMPLES

The following examples and test examples will illustrate the present invention further in detail but do not limit the scope thereof.

Example 1

Production of DNA (Plasmid) Comprising in a Molecule Both the Ligand-Responsive Reporter Gene and the Selective Marker Gene (1) Plasmid Containing a Recognition Sequence of an Allylhydrocarbon Receptor Genomic DNA was purified from a human-derived HepG2 cell using an Isogen reagent (manufactured by Nippon Gene) according to a method described in the protocol appended to the reagent. PCR was conducted by utilizing the purified genome as a template and using a forward primer: 5'-TTGAGCTAGGCACGCAAATA-3' and a reverse primer: 5'-GCTTTGATTGGCAGAGCACA-3', to amplify a DNA which has a nucleotide sequence (J. Biochem., 110, 232-236 (1991)) 750 bp to 1370 bp upstream from the upstream TATA box of a human CYP1A1 gene which contains XRE which is a recognition sequence of an allylhydrocarbon receptor. The amplified DNA was recovered, and the ends were smoothed by using a Blunting kit (manufactured by Takara Shuzo Co., Ltd.)(hereinafter, this DNA is referred to as XRE DNA).

Two oligonucleotides; 5'-GATCTCGACTATAAA-GAGGGCAGGCTGTCCTCAAGCGTCACCACGACTTCA-3' and 5'-AGCTTGAAGTCGTGGTGACGCTTAGAG-GACAGCCTGCCCTCTTTATAGT CGA-3' composed of nucleotide sequences derived from a nucleotide sequence near the TATA box of a mouse metallothionein I gene and the leader sequence (Genbank Accession No. J00605), were annealed to obtain a double stranded DNA, and T4 polynucleotide kinase was allowed to act thereon to phosphorylate the both ends thereof (hereinafter, this DNA is referred to as TATA DNA). On the other hand, a plasmid pGL3 (manufactured by Promega) containing a fire fly luciferase gene was digested with restriction enzymes Bgl II and Hind III, to this was further added Bacterial alkaline phosphatase (BAP) and the mixture was kept at 65° C. for 1 hour. Then, this incubated solution was subjected to electrophoresis using an agarose having a low melting point (Agarose L; manufactured by Nippon Gene) to recover DNA showing an electrophoretic movement corresponding to the length of the Bgl II-Hind III fragment containing a luciferase gene derived from pGL3. About 100 ng of this DNA and 1 μg of the above-mentioned TATA DNA were mixed and bonded via a T4 ligase to produce a plasmid pGL3-TATA.

Then, pGL3-TATA was digested with a restriction enzyme Sma I, to this was further added BAP, and the mixture was kept at 65° C. for 1 hour. This incubated solution was subjected to electrophoresis using an agarose gel having a low melting point, to recover DNA from the gel in the band portions. After about 100 ng of this DNA and about 1 μg of the above-mentioned XRE DNA were mixed and reacted with a T4 ligase, the reaction solution was introduced into an E. coli DH5α competent cell (manufactured by TOYOBO). The DNA of respective plasmids contained in several colonies of E. coli which showed ampicillin resistance were purified and were digested with restriction enzymes Kpn I and Xho I, such that the digested solution was analyzed by agarose gel electrophoresis. A plasmid having a structure in which one copy of about 600 bp DNA corresponding to the XRE DNA had been introduced into the Sma I site of pGL3-TATA was selected, and named pGL3-TATA-1A1.

Then, a plasmid, pUCSV-BSD (purchased from FUNA-KOSHI) was digested with BamHI, to prepare DNA coding a blastcidin S deaminase gene-expressing cassette. This DNA was mixed with the DNA obtained by digestion and BAP treatment of the above-mentioned plasmid pGL3-TATA-1A1, to obtain a mixture which was reacted with a T4 ligase, and the reaction solution was then introduced into an E. coli DH5α competent cell (manufactured by TOYOBO). From the resulted ampicillin resistant E. coli clones, plasmid DNAs were prepared and were digested with restriction enzyme Bam HI, such that the digested solution was analyzed by agarose gel electrophoresis. A plasmid having a structure in which the blastcidin S deaminase gene-expressing cassette had been inserted into the Bam HI cut site of the plasmid pGL3-TATA-1A1 was selected, and named plasmid pGL3-TATA-1A1-BSD.

(2) Plasmid Containing the Recognition Sequence of an Estrogen Receptor

An oligonucleotide comprising a nucleotide sequence (5'-TCGACAAAGTCAGGTCACAGTGACCTGATCAAG-3') at the upstream of a Xenopus-derived vitellogenin gene containing a recognition sequence of an estrogen receptor, and an oligonucleotide comprising a nucleotide sequence complimentary to the aforementioned nucleotide sequence were synthesized by a DNA synthesizer, and the products were annealed to obtain a double-stranded DNA (hereinafter, referred to as ERE DNA), then, a T4 ligase was reacted with the DNA to allow the double-stranded DNA to bond in tandem, T4 polynucleotide kinase was allowed to act on this to phosphorylate the both ends.

Then, the plasmid pGL3-TATA produced as described in the above-mentioned procedure (1) was digested with restriction enzyme Sma I, to this was further added BAP and the mixture was kept at 65° C. for one hour. This incubated solution was subjected to a low melting point agarose gel electrophoresis, to recover the DNA from the gel in the band portion. About 100 ng of this DNA and about 1 μg of the above-mentioned DNA obtained by binding the ERE DNA in tandem and phosphorylating the ends thereof were mixed to obtain a mixture which was reacted with a T4 ligase. The reaction solution was introduced into a E. coli DH5α competent cell (manufactured by TOYOBO). The DNAs of respective plasmids contained in several colonies of *E. coli* which showed ampicillin resistance were purified and were digested with restriction enzymes Kpn I and Xho I, and the digested solution was analyzed by agarose gel electrophoresis. A plasmid having a structure in which 5 copies of ERE DNAs had been introduced in tandem in the Sma I site of pGL3-TATA was selected, and this was named pGL3-TATA-ERE×5.

Then, a plasmid pUCSV-BSD (purchased from FUNAKOSHI) was digested with BamHI, to prepare DNA coding a blastcidin S deaminase gene-expressing cassette. This DNA was mixed with DNA obtained by the digestion with Bam HI and the BAP treatment of the above-mentioned plasmid pGL3-TATA-ERE×5, to obtain a mixture which was reacted with a T4 ligase and the reaction solution was then introduced into an *E. coli* DH5α competent cell. From the resulted ampicillin resistant *E. coli* clones, plasmid DNAs were prepared and were digested with restriction enzyme Bam HI, and the digested solution was analyzed by agarose gel electrophoresis. A plasmid having a structure in which the blastcidin S deaminase gene-expressing cassette had been inserted into the Bam HI cut site of the plasmid pGL3-TATA-ERE×5 was selected, and named plasmid pGL3-TATA-ERE×5-BSD.

Example 2

Production of DNA (Plasmid) Comprising on Same Molecule Both of Ligand-Responsive Reporter Gene and Selective Marker Gene First, a forward primer: 5'-CGGCAGATCTTCTTTAGT-TCTATGATGACAC-3' and a reverse primer: 5'-CG-GAAGCTTGATCTGCGGCACGCTGTTGA-3' were designed based on the HSV-tk promoter portion of a pTKβ (manufactured by Clone Tech) plasmid, and synthesized by a DNA synthesizer. Using these two primers, PCR was conducted by utilizing 1 ng of the plasmid pTKβ as a template, to obtain 185 bp DNA containing a nucleotide sequence from −131 base (transcription initiation point is +1) to +54 base in the HSV-tk promoter region. Portions near the 5' end and 3' end of this DNA contained, respectively, the Bgl II recognition site and Hind III recognition site introduced by the above-mentioned PCR primers. Then, this DNA was digested with Bgl II and Hind III, and then subjected to gel electrophoresis using an agarose having a low melting point [NusieveGTG (manufactured by FMC)], to recover the DNA from gel. On the other hand, a plasmid pGL (manufactured by Promega) containing a fire fly luciferase gene was digested with Bgl II and Hind III, to this was further added Bacterial alkaline phosphatase (BAP) and the mixture was kept at 65° C. for 1 hour. Then, this incubated solution was subjected to electrophoresis using an agarose having a low melting point (Agarose L; manufactured by Nippon Gene) and DNA showing an electrophoretic movement corresponding to the length of a Bgl II-Hind III fragment containing a luciferase gene derived from pGL3 was recovered. About 100 ng of this DNA was mixed with about 1 μg of the above-mentioned DNA of about 200 bp containing the HSV-tk promoter region prepared as described above, which was reacted with a T4 ligase, introduced into an *E. coli* DH5α competent cell (manufactured by TOYOBO). A plasmid was prepared from the resulting ampicillin-resistant clone, and a plasmid was selected therefrom in which one copy of the HSV-tk promoter had been introduced between the Bgl II-Hind III sites of pGL3, and was called pGL3-tk.

A T4 ligase was reacted with the ERE DNA prepared according to the description in Example 1 (2), allowing the double-stranded DNA to bind in tandem, and the T4 polynucleotide kinase was allowed to act thereon to phosphorylate the both ends.

The above-mentioned pGL3-tk was digested with a restriction enzyme, Sma I, to this was further added BAP and the mixture was kept at 65° C. for one hour. This incubated solution was subjected to electrophoresis using an agarose gel having a low melting point, to recover DNA from the gel in the band portion. About 100 ng of this DNA and about 1 μg of the above-mentioned DNA which had been bonded in tandem and of which ends had been phosphorylated were mixed to obtain a mixture which was reacted with a T4 ligase. The reaction solution was introduced into a *E. coli* DH5α competent cell (manufactured by TOYOBO). The DNAs of respective plasmids contained in several colonies of *E. coli* which showed ampicillin resistance were purified and were digested with restriction enzymes Kpn I and Xho I and the digested solution was analyzed by agarose gel electrophoresis. A plasmid having a structure in which 5 copies of ERE DNAs had been introduced in tandem in the Sma I site of pGL3-tk was selected, and this was named pGL3-tk-ERE×5.

Then, a plasmid PUCSV-BSD (purchased from FUNAKOSHI) was digested with BamHI, to prepare DNA coding a blastcidin S deaminase gene-expressing cassette. This DNA was mixed with DNA obtained by the digestion with Bam HI and the BAP treatment of the above-mentioned plasmid pGL3-tk-ERE×5 to obtain a mixture which was reacted with a T4 ligase. The reaction solution was introduced into an *E. coli* DH5α competent cell. From the resulting ampicillin-resistant *E. coli* clones, plasmid DNAs were prepared which were digested with a restriction enzyme Bam HI, and the digested solution was analyzed by agarose gel electrophoresis. A plasmid having a structure in which the blastcidin S deaminase gene-expressing cassette had been inserted into the Bam HI cut site of the plasmid pGL3-tk-ERE×5 was selected, and named plasmid pGL3-tk-ERE×5-BSD. This plasmid was used in the comparative tests below.

Example 3

Production of Ligand-Responsive Transcription Control Factor-Expressing Plasmid (1) Estrogen Receptor α Expressing Plasmid A forward primer: 5'-CCTGCGGGGACACGGTCTG-CACCCTGCCCGCGGCC-3' and a reverse primer: 5'-CAGGGAGCTCTCAGACTGTGGCAGG-GAAACCCTCT-3' were designed, based on the nucleotide sequence of an estrogen receptor a gene published under Genbank Accession No. M12674, and were synthesized by a DNA synthesizer (Model 394 manufactured by Applied Biosystems), to obtain cDNA coding a human estrogen receptor α.

Then, the above-mentioned primers, each in an amount of 10 pmol, were added to 10 ng of human hepatic cDNA (Quick clone cDNA# 7113 manufactured by Clone Tech) as a template, and a PCR reaction was conducted using a LA-Taq polymerase (manufactured by Takara Shuzo Co., Ltd.) and the buffer appended with the enzyme, in a reaction solution amount of 50 μl. In this reaction, the reaction solution was kept at 95° C. for 1 minute and then kept at 68° C. for three minutes, and this cycle was repeated 35-times, using PCR system 9700 (manufactured by Applied Biosystems). Then, the whole reaction solution was subjected to agarose gel electrophoresis using an agarose having a low melting point (Agarose L; manufactured by Nippon Gene). That the band having the size expected from known sequences had been amplified was confirmed, and the DNA was then recovered from the band, and a sample for direct sequence was prepared using this DNA and Die Terminator Sequence kit FS (manufactured by Applied Biosystems). This was subjected to nucleotide sequence analysis using Auto Sequencer (Model 377 manufactured by Applied Biosystems), to confirm the nucleotide sequence.

PCR using a forward primer: 5'-CCCAGCCACCATGAC-CATGACCCTCCACACCAAAGCATCT-3' and a reverse primer: 5'-CAGGGAGCTCTCAGACTGTGGCAGG-GAAACCCTCT-3' was conducted using as a template about 100 ng of the DNA obtained as described above, to prepare a DNA containing a Kozak consensus sequence directly upstream from the translation initiation codon ATG of an estrogen receptor α gene. Namely, 0.1 μg of estrogen receptor a cDNA as a template, LA-Taq polymerase (manufactured by Takara Shuzo Co., Ltd.), reaction buffer added to the enzyme and the above-mentioned primers, each in 10 pmol, were mixed to obtain a reaction solution in an amount of 50 μl, and the solution was kept at 95° C. for 1 minute and then kept at 68° C. for 3 minutes, and this cycle was repeated 20-times. The thus amplified product was separated and recovered by a lower temperature agarose gel electrophoresis method. Then, about 1 μg of this product was treated with a DNA Blunting kit (manufactured by Takara Shuzo Co., Ltd.) to blunt the ends thereof, and were reacted with T4 polynucleotide kinase for phosphorylation of the ends thereof. This DNA was treated with phenol and was purified by an ethanol precipitation method, and the whole purified product was used as insert DNA for producing an expression plasmid below.

A pRC/RSV (manufactured by Invitrogen) containing a RSV promoter and a neomycin-resistant gene was digested with a restriction enzyme Hind III, to this was further added BAP and the mixture was kept at 65° C. for 1 hour. Then this was purified by treatment with phenol and precipitation with ethanol, and the ends thereof were then blunted by treating with a DNA Blunting kit (manufactured by Takara Shuzo Co., Ltd.) and subjected to agarose gel electrophoresis using an agarose having lower melting temperature (Agarose L, manufactured by Nippon Gene), and the DNA was recovered from the band portion. About 100 ng of the recovered vector DNA and the whole amount of the above-mentioned isocyanate were mixed, to this was added a T4 ligase, and that was reacted. This reaction solution was introduced into an *E. coli* DH5α competent cell, and plasmid DNA was then prepared from a colony showing ampicillin-resistance, and the nucleotide sequence thereof was determined by a die terminator method using an ABI model 377 type Auto Sequencer. The resulting nucleotide sequence was compared with a nucleotide sequence obtained in the above-mentioned direct sequence, and a plasmid providing confirmation of complete accordance between nucleotide sequences in the translation region was selected, and named pRC/RSV-hERα Kozak.

Example 4

Production of the Cell of the Present Invention

The DNA of the plasmid pGL3-TATA-EREx5-BSD produced in Example 1 (2) or the plasmid pGL3-tk-EREx5-BSD produced in Example 2, and DNA of the expression plasmid pRC/RSV-hERα Kozak produced in Example 3 were linearized, respectively, and introduced into a NIH3T3 cell, and a cell which can be used for measuring the transcription activity of a gene receiving the transcription control by an estrogen receptor was produced.

First, each of the DNA of the plasmid pGL3-TATA-EREx 5-BSD, the DNA of the plasmid pGL3-tk-EREx5-BSD and the DNA of the plasmid pRC/RSV-hERα Kozak was digested with Sal I.

NIH3T3 cells were cultured using a dish (manufactured by Falcon) having a diameter of about 10 cm in the presence of 5% $CO_2$ at 37° C. using DMEM medium containing 10% FBS (manufactured by Nissui Pharmaceutical Co., Ltd.). About $5 \times 10^5$ cells were cultured, and next day, into this cell was introduced DNAs of the above-mentioned linearized plasmids by a lipofection method using lipofectamine (manufactured by GIBCO) in the following combination: 1̂ pGL3-TATA-EREx5-BSD and pRC/RSV-hERαKozak and 2̂ pGL3-tk-EREx5-BSD and pRC/RSV-hERα Kozak. Conditions of the lipofection method include, according to the description of a manual appended to lipofectamine, a treating time of 5 hours, a total amount of the linearized plasmid DNAs of 7 μg (respectively 3.5 μg)/dish, and an amount of lipofectamine of 42 μl/dish. After the lipofection treatment, the medium was substituted with DMEM medium containing 10% FBS and was cultured for about 36 hours. Then, the cell was removed from the dish by trypsinization and recovered, and was then transferred to a culturing vessel comprising a medium containing G418 at a final concentration of 800 μg/ml and blasticidin S at a final concentration of 16 μg/ml, and cultured for about one month while exchanging the medium with a new medium (containing the above-mentioned selective chemicals) at every 3 to 4 days. The emerged cell colonies having a diameter of from 1 mm to several mm were transferred respectively to a 96-well plate (manufactured by Bell Told) to which the medium had been previously separated and poured, and were cultured further. When the cell proliferated to extent occupying half or more of the bottom surface of the well (about 5 days after the transfer), the cells were removed by trypsinization and recovered, and divided into three portions and transferred to three new 96-well view plates. On one plate, passage and culturing were continued, as a master plate. On one of the remaining two plates, 17β estradiol dissolved in DMSO was added to a final concentration of 10 nM, and on the other plate, DMSO of the same volume as that of the above-mentioned 17β estradiol solution was added, and both of them were cultured for 2 days. Then, with these two plates, the medium was removed from the well, cells adhered to vessel walls were washed with PBS(−) twice, then, PGC 50 (manufactured by Toyo Ink) diluted 5-fold was added in an amount of 20 μl per well, and that was left for 30 minutes at room temperature. These plates were set in a Luminometer LB96P (manufactured by Bell Told) equipped with an automated enzyme substrate injector, and 50 μl of a substrate solution, PGL100 (manufactured by Toyo Ink) was automatically separated and poured, and the luciferase activity was measured.

Among transformed cells obtained by introducing DNA of (1) pGL3-TATA-EREx5-BSD and pRC/RSV-hERα Kozak, 288 clones were subjected to the above-mentioned test. Regarding the ratio of the luciferase activity in a system containing 10 nM of added 17β estradiol to the luciferase activity of a system containing no added 17β estradiol, the number of clones having a ratio of not more than 2-fold was 50, the number of clones having a ratio of not less than 2-fold and not more than 5-fold was 40, the number of clones having a ratio of not less than 5-fold and not more than 10-fold was 56, the number of clones having a ratio of not less than 10-fold and not more than 50-fold was 118, the number of clones having a ratio of not less than 50-fold and not more than 100-fold was 15, and the number of clones having a ratio of not less than 100-fold was 9.

On the other hand, among transformed cells obtained by introducing DNA of 2 pGL3-tk-EREx5-BSD and pRC/RSV-hERα Kozak, 192 clones were subjected to the above-mentioned test. Regarding the ratio of the luciferase activity in a system containing 10 nM of added 17β estradiol to the luciferase activity of a system containing no added 17β estradiol, the number of clones having a ratio of not more than 2-fold was 100, the number of clones having a ratio of not less than 2-fold and not more than 5-fold was 64, the number of clones having a ratio of not less than 5-fold and not more than 10-fold was 25, the number of clones having a ratio of not less than 10-fold and not more than 50-fold was 3, the number of clones having a ratio of not less than 50-fold and not more than 100-fold was 0, and the number of clones having a ratio of not less than 100-fold was 0.

Example 5

Production of the Cell of the Present Invention

The DNA of the plasmid pGL3-TATA-1A1-BSD produced in Example 1 (1) was linearized and introduced into a human-derived MCF7 cell which expresses an allylhydrocarbon receptor, to fabricate a cell of the present invention which can be used for measuring the transcription activity of a gene receiving the transcription control by the allylhydrocarbon receptor.

First, the DNA of the plasmid pGL3-TATA-1A1-BSD was digested with Sal I.

Further, the MCF7 cell was cultured using a dish (manufactured by Falcon) having a diameter of about 10 cm in the presence of 5% $CO_2$ at 37° C. using DMEM medium (manufactured by Nissui Pharmaceutical Co., Ltd.) containing 10% FBS. About $5 \times 10^5$ cells were cultured, and next day, into this cell was introduced the DNA of the above-mentioned linearized plasmid pGL3-TATA-1A-BSD by a lipofection method using lipofectamine (manufactured by GIBCO). Conditions of the lipofection method include, according to the description of a manual appended with the lipofectamine, a treating time of 5 hours, a total amount of the linearized plasmid DNAs of 7 μg/dish, and an amount of lipofectamine of 56 μl/dish. After the lipofection treatment, the medium was substituted with DMEM medium containing 10% FBS and was cultured for about 36 hours. Then, the cell was removed from the dish by trypsinization and recovered and transferred to a culturing vessel comprising a medium containing an added cell selective chemical, blastcidin S, to a final concentration of 16 μg/ml, and cultured for about one month and a half while exchanging the medium with a new medium (containing the selective chemical) at every 3 to 4 days. The emerged cell colonies having a diameter of from 1 mm to several mm were transferred respectively to a 96-well plate (manufactured by Bell Told) to which the medium had been previously separated and poured, and that was further cultured. When the cell proliferated to an extent of occupying half or more of the bottom surface of the well (about 5 days after the transfer), the cells were removed by trypsinization and recovered, and divided into three portions and transferred on three new 96-well view plates. On one plate, passage and culturing were continued, as a master plate. On one of the remaining two plates, 3-methylcholanthrene dissolved in DMSO was added to a final concentration of 50 nM, and on the other plate, DMSO of the same volume as that of the 3-methylcholanthrene solution was added, and both of them were cultured for 2 days. Then, with these two plates, the medium was removed from the well, cells adhered to vessel walls were washed with PBS(-) twice, and PGC 50 (manufactured by Toyo Ink) diluted by 5-fold was then added in an amount of 20 μl per well, and that was left for 30 minutes at room temperature. These plates were set in a Luminometer LB96P (manufactured by Bell Told) equipped with an automated enzyme substrate injector, and 50 μl of a substrate solution, PGL100 (manufactured by Toyo Ink) was automatically separated and poured, and the luciferase activity was measured. A cell providing 2-fold or more higher luciferase activity in the system containing added 3-methylcholanthrene than in the system containing no added 3-methylcholanthrene was added was selected.

Example 6

Production of Reporter Plasmid for Obtaining Control Cell (1) Plasmid in which Reporter Gene is Connected Under Transcription Control of a TK Promoter First, a plasmid, pRL-TK (manufactured by Promega) was digested with Hind III and Bgl II, and was subjected to electrophoresis using an agarose having a low melting point (Agarose L; manufactured by Nippon Gene), and a 760 bp DNA containing a TK promoter was recovered. Then plasmid pGL3 was digested with Hind III and Bgl II, to this was further added BAP, and the mixture was kept at 65° C. for 1 hour, and this incubated solution was subjected to electrophoresis using agarose having a low melting point, to recover DNA showing an electrophoretic movement corresponding to the length of a Bgl II-Hind III fragment containing a luciferase gene derived from pGL3. About 0.1 μg of this DNA was mixed with about 0.2 μg of the above-mentioned DNA containing a TK promoter, and the mixture was reacted with a T4 ligase and introduced into an E. coli DH5α competent cell (manufactured by TOYOBO). Plasmid DNA was prepared from the resulting ampicillin-resistant clone, and was digested with restriction enzymes Hind III and Bgl II, and the digested solution was analyzed by agarose gel electrophoresis. A plasmid having a structure in which the above-described DNA containing a TK promoter had been introduced between the Hind III site and the Bgl II site of pGL3 was selected and was named plasmid pGL3-TK. Then, the DNA of this pGL3-TK was digested with Bam HI, to this was further added BAP and the mixture was kept at 65° C. for one hour, and this incubated solution was subjected to electrophoresis using an agarose gel having a low melting point, and the detection of a single band was confirmed and the DNA was recovered from the gel of the band portion. A plasmid having a structure in which a blastcidin S deaminase gene-expressing cassette had been inserted to the Bam HI cut site of pGL3 by connecting, via a T4 ligase, and the above-mentioned DNA with the DNA coding the blastcidin S deaminase gene-expressing cassette which had been prepared by digesting a plasmid pUCSV-BSD (purchased from FUNAKOSHI) with Bam HI was selected, to obtain a plasmid pCL3-TK-BSD.

(2) Plasmid in which Reporter Gene is Connected Under Transcription Control of RAV Promoter First, a plasmid, pRC/RSV was digested with Bgl II and Hind III, subjected to electrophoresis using agarose having a low melting point (Agarose L; manufactured by Nippon Gene), and 594 bp DNA containing a RSV promoter was recovered. Then plasmid pGL3 was digested with Hind III and Bgl II, to this was further added BAP, the mixture was kept at 65° C. for 1 hour, and then this incubated solution was subjected to electrophoresis using an agarose having a low melting point, to recover DNA showing an electrophoretic movement corresponding to the length of a Bgl II-Hind III fragment containing a luciferase gene derived from pGL3. About 0.1 μg of this DNA was mixed with about 1 μg of the above-mentioned DNA containing a RSV promoter, which was reacted with a T4 ligase, and was then introduced into an *E. coli* DH5α competent cell (manufactured by TOYOBO). Plasmid DNA was prepared from the resulting ampicillin-resistant clone and was digested with restriction enzymes Hind III and Bgl II, and the digested solution was analyzed by agarose gel electrophoresis. A plasmid having a structure in which the above-described DNA containing a RSV promoter had been introduced between the Hind III site and the Bgl II site of pGL3 was selected, and was called plasmid pGL3-RSV. Then, this plasmid was digested with Bam HI, to this was further added BAP and the mixture was kept at 65° C. for one hour, then, this incubated solution was subjected to electrophoresis using an agarose gel having a low melting point, and detection of a single band was confirmed before recovering DNA from gel of the band portion. A plasmid having a structure in which a blastcidin S deaminase gene-expressing cassette had been inserted to the Bam HI cut site of pGL3-RSV by connecting, via a T4 ligase, the above-mentioned DNA with DNA coding the blastcidin S deaminase gene-expressing cassette which had been prepared by digesting the plasmid pUCSV-BSD (purchased from FUNAKOSHI) with Bam HI was selected, to obtain a plasmid, pCL3-RSV-BSD.

Example 7

Production of Control Cell

The plasmid pGL3-TK prepared in Example 6 (1) was digested with Sal I and the plasmid pGL3-RSV prepared in Example 6 (2) was digested with Xho I, respectively A HeLa cell was cultured using a dish (manufactured by Falcon) having a diameter of about 10 cm in the presence of 5% $CO_2$ at 37° C. using DMEM medium containing 10% FBS (manufactured by Nissui Pharmaceutical Co., Ltd.). About $5 \times 10^5$ cells were cultured, and next day, into this cell was introduced the above-mentioned linearized plasmid pGL3-RSV or pGL3-TK by a lipofection method using lipofectamine (manufactured by GIBCO). Conditions of the lipofection method include, according to the description of a manual appended to lipofectamine, a treating time of 5 hours, an amount of the linearized plasmid DNA of 7 μg/dish, and an amount of lipofectamine of 21 μl/dish. After the lipofection treatment, the medium was substituted with DMEM medium containing 10% FBS and was cultured for about 36 hours. Then, the cell was removed from the dish by trypsinization and recovered and transferred to a culturing vessel comprising a medium containing the added cell selective chemical blastcidin S to a final concentration of 16 μg/ml, and cultured for one month while exchanging the medium with a new medium (containing the selective chemical) at every 3 to 4 days. The emerged cell colonies having a diameter of from 1 mm to several mm were transferred respectively to a 96-well plate (manufactured by Bell Told) to which the medium had been previously separated and poured, and that was cultured further. When the cell proliferated to an extent of occupying half or more of the bottom surface of the well (5 days after transfer), the cell was removed by trypsinization and recovered, and divided into two portions and transferred to two new 96-well view plates. On one plate, passage and culturing were continued, as a master plate. On one of the remaining two plates, the medium was removed from the well, cells adhered to vessel walls were washed with PBS(-) twice, and PGC 50 (manufactured by Toyo Ink) diluted 5-fold was then added in an amount of 20 μl per well, and that was left for 30 minutes at room temperature. These plates were set in a Luminometer LB96P (manufactured by Bell Told) equipped with an automated enzyme substrate injector, and 50 μl of a substrate solution, PGL100 (manufactured by Toyo Ink) was automatically separated and poured, and luciferase activity was measured. A clone showing luciferase activity which provides higher measured light emitting value than that in a well containing only an added measuring reagent, was selected as a control cell.

Test Example 1

Reporter Assay Using Cell of the Present Invention

A medium prepared by addition to phenol read-free MEM medium (manufactured by Nissui Pharmaceutical Co., Ltd.), of charcoal dextran-treated FBS so as to give a final concentration of 10% was used, and a cell of the present invention prepared as described in Example 4 or 5 was added at about $2 \times 10^4$ cells/well to a 96-well plate used for measuring luciferase light emission and for culturing (#3903, manufactured by Corning Coaster), and that was cultured overnight. Then, to this cell was added a chemical substance dissolved in DMSO. Therein, the dissolving solution was prepared and added, so that the final concentration of the chemical substance changed step-wise through the respective test districts in which the final DMSO amounts in the culturing solution in all of the test districts coincided at 0.1%. A control district added thereto only a solvent (DMSO) was provided as a system containing no added chemical substance, and a positive control district containing an added positive control chemical substance was also provided.

The cell containing the added chemical substance was cultured, and the medium was removed 36 hours after addition of the chemical substance, and the cell was washed twice with PBS (-), and PGC 50 (manufactured by Toyo Ink) diluted 5-fold was added in an amount of 20 pd per well, and that was left for 30 minutes at room temperature. This plate was set in a Luminometer LB96P (manufactured by Bell Told) equipped with an automated enzyme substrate injector, and 50 μl of the substrate solution, PGL100 (manufactured by Toyo Ink) was automatically separated and poured, and the luciferase activity was measured.

The agonist activity of genistein over the estrogen receptor α was measured using the cell of the present invention prepared in Example 4. The results are shown in FIG. 1. Increase in the luciferase activity by addition of genistein at a final concentration of 1 pM was recognized.

Thus, the agonist activity of a chemical substance over the intended ligand-responsive transcription control factor can be measured.

On the other hand, the antagonist activity of the chemical substance over the intended ligand-responsive transcription control factor can be measured, by adding a ligand of the intended ligand-responsive transcription control factor to each test district so as to give a concentration around an $EC_{50}$ value, together with the chemical substance, and by conducting the test in a similar manner as described above.

Further, it may also be permissible that a similar measurement is conducted using the control cell produced as described in Example 7 and the test results obtained as described above are corrected based on the measured results.

Example 8

Production of Ligand-Responsive Transcription Control Factor-Expressing Plasmid (1) Estrogen Receptor β

For obtaining cDNA which codes human estrogen receptor β comprising 530 amino acids, a forward primer: 5'-TTGAGTTACTGAGTCCGATGAATGTGCT-TGCTCTG-3' and a reverse primer: 5'-AAATGAGGGAC-CACACAGCAGAAAGATGAAGCCCA-3' were designed and synthesized with a DNA synthesizer (Model 394 manufactured by Applied Biosystems)

Then, the above-mentioned primers each in an amount of 10 pmol were added to 10 ng of human brain cDNA (Quick clone cDNA# 7187-1 manufactured by Clone Tech) as a template and a PCR reaction was conducted using a LA-Taq polymerase (manufactured by Takara Shuzo Co., Ltd.) and a buffer appended with the enzyme, in a reaction solution amount of 50 µl. In this reaction, the reaction solution was kept at 95° C. for 1 minute and then kept at 68° C. for three minutes, and this cycle was repeated 35-times, using a PCR system 9700 (manufactured by Applied Biosystems). Then, the whole reaction solution was subjected to agarose gel electrophoresis using an agarose having a low melting point (Agarose L; manufactured by Nippon Gene). That the band having a size expected from the known sequence had been amplified was confirmed, and then DNA was recovered from the band, and a sample for direct sequence was prepared using this DNA and a Die Terminator Sequence kit FS (manufactured by Applied Biosystems). This was subjected to nucleotide sequence analysis using Auto Sequencer (Model 377 manufactured by Applied Biosystems), to confirm the nucleotide sequence.

PCR using a forward primer: 5'-GCCGCGGCCGC-CCAGCCACCATGGATATAAAAAACTCAC-CATCTAGCCT TAATTC-3' and a reverse primer: 5'-GGGTCTAGAAATGAGGGACCACACAGCA-GAAAGATGAAGCCCA-3' was conducted by using as a template about 100 ng of the DNA obtained as described above, to prepare a DNA containing a Kozak consensus sequence directly upstream from the translation initiation codon ATG of an estrogen receptor β gene. Namely, 0.1 µg of estrogen receptor a cDNA as a template, LA-Taq polymerase (manufactured by Takara Shuzo Co., Ltd.), reaction buffer appended with the enzyme and the above-mentioned primers each in 10 pmol were mixed to obtain a reaction solution in an amount of 50 µl, and the solution was kept at 95° C. for 1 minute and then kept at 68° C. for 3 minutes, and this cycle was repeated 20-times. The thus amplified product was separated and recovered by a lower temperature agarose gel electrophoresis method. Then, about 1 µg of this product was treated with a DNA Blunting kit (manufactured by Takara Shuzo Co., Ltd.) to blunt the ends thereof, which were reacted with T4 polynucleotide kinase for phosphorylation of the ends thereof. This DNA was treated with phenol and was then purified by an ethanol precipitation method, and the whole purified product was used as an insert DNA for producing an expression plasmid.

A pRC/RSV (manufactured by Invitrogen) containing a RSV promoter and a neomycin-resistant gene was digested with a restriction enzyme Hind III, to this was further added BAP and the mixture was kept at 65° C. for 1 hour. Then this was purified by treatment with phenol and precipitation with ethanol, and the ends thereof were then blunted by treating with a DNA Blunting kit (manufactured by Takara Shuzo Co., Ltd.), and subjected to agarose gel electrophoresis using an agarose having lower melting temperature (Agarose L, manufactured by Nippon Gene), and a DNA was recovered from the band portion. About 100 ng of the recovered vector DNA and the whole amount of the above-mentioned inserted DNA were mixed, to this was added a T4 ligase and that was reacted. This reaction solution was introduced into an E. coli DH5α competent cell, and plasmid DNA was then prepared from the colony showing ampicillin-resistance, and the nucleotide sequence thereof was determined by a die terminator method using an ABI model 377 type Auto Sequencer. The resulting nucleotide sequence was compared with a nucleotide sequence obtained in the above-mentioned direct sequence, and a plasmid providing confirmation of complete accordance between nucleotide sequences in the translation region was selected, and named pRC/RSV-hER1β Kozak.

Example 9

Production of Cell of the Present Invention (2) Estrogen Receptor β

DNA of the plasmid pGL3-TATA-EREx5-BSD produced in Example 1 (2) and DNA of the expression plasmid pRC/RSV-hERβ Kozak produced in Example 8 were linearized respectively and introduced into a human-derived HeLa cell, to obtain a cell of the present invention which can be used for measuring the transcription activity of a gene receiving the transcription control by the estrogen receptor β. Namely, a similar procedure was conducted as in Example 4 except that an expression plasmid pRC/RSV-hERβ Kozak of the estrogen receptor β was used instead of the expression plasmid pRC/RSV-hERα Kozak of the estrogen receptor α in Example 4. The luciferase activity of the resulting transformed cell was measured in the presence of 17β estradiol as in Example 4 and in the absence of 17β estradiol, and a cell which shows higher luciferase activity by 2-fold or more in a system containing added 17β estradiol than in a system containing no added 17β estradiol was selected.

Test Example 2

Reporter Assay Using Cell of the Present Invention

A medium prepared by addition to phenol read-free MEM medium (manufactured by Nissui Pharmaceutical Co., Ltd.) of charcoal dextran-treated FBS so as to give a final concentration of 10% was used, and a cell of the present invention prepared as described in Example 4 or 10 was added to a 96-well plate used for measuring luciferase light emission and for culturing (#3903, manufactured by Corning Coaster) at about $2 \times 10^4$ cells/well, and that was cultured overnight. Then, to this cell was added 17β estradiol dissolved in DMSO. Therein, the dissolving solution was prepared and added, so that the final concentration of 17β estradiol increased, each by 10-fold, through the respective test districts in which the final DMSO amounts in the culturing solution in all of the test districts coincided at 0.1%. A control district having added thereto only a solvent (DMSO) was provided as a system containing no added chemical substance.

These cells were cultured, and the medium was removed 36 hours after the addition of 17β estradiol, and the cells were washed twice with PBS (−) and PGC 50 (manufactured by Toyo Ink) diluted 5-fold was then added in an amount of 20 µl per well, and those were left for 30 minutes at room temperature. This plate was set in a Luminometer LB96P (manufactured by Bell Told) equipped with an automated enzyme substrate injector, and 50 µl of a substrate solution PGL100 (manufactured by Toyo Ink) was automatically separated and poured, and the luciferase activity was measured. Increase in luciferase activity along with the increase in the concentration of 17β estradiol added to the cell was recognized, in both the cell of the present invention for measuring the transcription activity of a gene receiving the transcription control of estrogen receptor α and the cell of the present invention for measuring the transcription activity of a gene receiving the transcription control of estrogen receptor β.

In a similar manner as described above, the agonist activity of a chemical substance over the intended estrogen receptor can be measured by adding a chemical substance instead of 17β estradiol to each test district and conducting the test.

On the other hand, the antagonist activity of a chemical substance on the intended estrogen receptor can be measured by adding, together with a chemical substance, 17β estradiol to each test district so as to give a concentration around $EC_{50}$ value, and conducting a test in a similar manner as described above.

Example 10

Production of DNA (Plasmid) Comprising in Molecule, the Ligand-Responsive Reporter Gene and the Selective Marker Gene The DNA in a region containing an androgen receptor recognition sequence derived from the LTR of a mouse mammary tumor virus (MMTV) was produced. Plasmid pMSG (manufactured by Pharmacia) was digested with restriction enzymes Hind III and Sac I, to obtain a 1080 bp DNA corresponding to a part of the MMTV-LTR region (hereinafter, referred to as ARE-A DNA). Further, plasmid pMSG was digested with restriction enzymes Hind III and Sma I, to obtain a 1463 bp DNA corresponding to a part of the MMTV-LTR region (hereinafter, referred to as ARE-B DNA). Both DNAs were treated with a Blunting kit (manufactured by Takara Shuzo Co., Ltd.).

Two oligonucleotides; 5'-GATCTCGACTATAAA-GAGGGCAGGCTGTCCTCTAAGCGTCACCACGACT TCA-3' and 5'-AGCTTGAAGTCGTGGTGACGCTTA-GAGGACAGCCTGCCCTCTTTATAGT CGA-3' having nucleotide sequences derived from a nucleotide sequence near the TATA box of a mouse metallothionein I gene and the leader sequence were annealed to obtain a double stranded DNA, and T4 polynucleotide kinase was allowed to act thereon to phosphorylate both ends thereof (hereinafter, this DNA is referred to as TATA DNA). On the other hand, a plasmid pGL3 (manufactured by Promega) containing a fire fly luciferase gene was digested with restriction enzymes Bgl II and Hind III, to this was further added Bacterial alkaline phosphatase (BAP) and the mixture was kept at 65° C. for 1 hour. Then, this incubated solution was subjected to electrophoresis using agarose having a low melting point (Agarose L; manufactured by Nippon Gene), and DNA was recovered from the gel of the band portion. About 100 ng of this DNA and 1 µg of the above-mentioned TATA DNA were mixed and bonded via a T4 ligase to produce a plasmid pGL3-TATA.

Then, the pGL3-TATA was digested with a restriction enzyme Sma I, to this was further added BAP, and the mixture was kept at 65° C. for 1 hour. This incubated solution was subjected to electrophoresis using an agarose gel having a low melting point, and DNA was recovered from the gel of the band portions. About 100 ng of this DNA and about 1 µg of the above-mentioned ARE-A DNA were mixed and reacted with a T4 ligase, and then the reaction solution was introduced into a E. coli DH5α competent cell (manufactured by TOYOBO). The DNA of the respective plasmid contained in several colonies of E. coli which showed ampicillin resistance were purified and were digested with restriction enzymes Kpn I and Xho I, and the digested solution was analyzed by agarose gel electrophoresis. A plasmid having a structure in which one copy of ARE-A DNA had been introduced in the Sma I site of pGL3-TATA was selected, and named pGL3-TATA-MMTV.

On the other hand, a plasmid pGL3 (manufactured by Promega) containing a fire fly luciferase gene was digested with restriction enzymes Bgl II and Hind III, to this was further added Bacterial alkaline phosphatase (BAP) and kept at 65° C. for 1 hour, and this was further treated with a Blunting kit (manufactured by Takara Shuzo Co., Ltd.). Then, this DNA was subjected to electrophoresis using an agarose having a low melting point (Agarose L; manufactured by Nippon Gene), and the DNA was recovered from the gel of the band portion. About 100 ng of this DNA and 1 µg of the above-mentioned ARE-B DNA were mixed and bonded via a T4 ligase, and the reaction solution was introduced into an E. coli DH5α competent cell. The DNA of the respective plasmid contained in several colonies of E. coli which showed ampicillin resistance were purified and were digested with restriction enzymes Kpn I and Cla1, and the digested solution was analyzed by agarose gel electrophoresis. A plasmid having a structure in which only one copy of ARE-B DNA had been introduced between the Bgl II site and the Hind III site of the pGL3 bector was selected, and named pGL3-MMTV.

Then, a plasmid pUCSV-BSD (purchased from FUNAKO-SHI) was digested with BamHI, to prepare DNA coding a blastcidin S deaminase gene-expressing cassette. This DNA was mixed with DNA obtained by the digestion with Bam HI and the BAP treatment of the above-mentioned plasmid pGL3-TATA-MMTV or pGL3-MMTV to obtain a mixture which was reacted with a T4 ligase, and the reaction solution was introduced into an E. coli DH5α competent cell. From the resulted ampicillin resistant E. coli clones, plasmid DNA was prepared was digested with restriction enzyme Bam HI, and the digested solutions were analyzed by agarose gel electrophoresis. A plasmid having a structure in which the blastcidin S deaminase gene-expressing cassette had been inserted into the Bam HI site was selected, and named plasmid pGL3-TATA-MMTV-BSD and pGL3-MMTV-BSD, respectively.

Example 11

Production of Ligand-Responsive Transcription Control Factor-Expressing Plasmid (1) Androgen Receptor Expression Plasmid A forward primer: 5'-GAGGCGGGGTAAGGGAAG-TAGGTGGAAGATTCAGC-3' and a reverse primer: 5'-GGGTGGGGAAATAGGGTTTCCAATGCT-TCACTGGG-3' were designed, based on the nucleotide sequence of an estrogen receptor gene published under Genbank Accession No. M23263, and synthesized by a DNA synthesizer (Model 394 manufactured by Applied Biosystems), to obtain cDNA coding a human androgen receptor.

Then, the above-mentioned primers each in an amount of 10 pmol were added to 10 ng of human prostate cDNA (Quick clone cDNA# 7123-1 manufactured by Clone Tech) as a template, and a PCR reaction was conducted by using a LA-Taq polymerase (manufactured by Takara Shuzo Co., Ltd.) and a buffer added to the enzyme, in a reaction solution amount of 50 µl. In this reaction, the reaction solution was kept at 95° C. for 1 minute and then kept at 68° C. for three minutes, and this cycle was repeated 35-times, using a PCR system 9700 (manufactured by Applied Biosystems). Then, the whole reaction solution was subjected to agarose gel electrophoresis using an agarose having a low melting point (Agarose L; manufactured by Nippon Gene). That the band having a size expected from known sequences had been amplified was confirmed by ethidium bromide staining, and the DNA was recovered from the band, and a sample for direct sequence was prepared by using this DNA and Die Terminator Sequence kit FS (manufactured by Applied Biosystems). This was subjected to nucleotide sequence analysis using an Auto Sequencer (Model 377 manufactured by Applied Biosystems), to confirm the nucleotide sequence.

PCR using a forward primer: 5'-CCCAGCCACCATG-GAAGTGCAGTTAGGGCTGGGAAGGGTC-3' and a reverse primer: 5'-GGGTGGGGAAATAGGGTTTCCAAT-GCTTCACTGGG-3' was conducted using as a template about 100 ng of the DNA obtained as described above, to prepare DNA containing a Kozak consensus sequence added directly before the translation initiation codon, ATG of an androgen receptor gene. Namely, 0.1 µg of androgen receptor cDNA as a template, LA-Taq polymerase (manufactured by Takara Shuzo Co., Ltd.), reaction buffer appended with the enzyme, and the above-mentioned primers each in 10 pmol were mixed to obtain a reaction solution in an amount of 50 µl, and the solution was kept at 95° C. for 1 minute and then kept at 68° C. for 3 minutes, and this cycle was repeated 20-times. The amplified product thus obtained was separated and recovered by a lower temperature agarose gel electrophoresis method. Then, about 1 µg of this product was treated with a DNA Blunting kit (manufactured by Takara Shuzo Co., Ltd.) to blunt the ends thereof, which were reacted with T4 polynucleotide kinase for the phosphorylation of the ends thereof. This DNA was treated with phenol and purified by an ethanol precipitation method, and the whole purified product was used as an insert DNA for producing the following expression plasmid.

A pRC/RSV (manufactured by Invitrogen) containing a RSV promoter and a neomycin-resistant gene was digested with a restriction enzyme Hind III, to this was further added BAP and the mixture was kept at 65° C. for 1 hour. Then this was purified by treatment with phenol and precipitation with ethanol, and the ends thereof were blunted by treating with a Blunting kit (manufactured by Takara Shuzo Co., Ltd.), and subjected to agarose gel electrophoresis using an agarose having lower melting temperature (Agarose L, manufactured by Nippon Gene), and DNA was recovered from gel of the band portion. About 100 ng of the recovered vector DNA and the whole amount of the above-mentioned inserted DNA were mixed, to this was added a T4 ligase and they were reacted. This reaction solution was introduced into an *E. coli* DH5α competent cell, and the plasmid DNA was then prepared from a colony showing ampicillin-resistance, and the nucleotide sequence thereof was determined by a die terminator method using ABI model 377 type Auto Sequencer. The resulting nucleotide sequence was compared with a nucleotide sequence obtained in the above-mentioned direct sequence, and a plasmid providing confirmation of complete accordance between nucleotide sequences in the translation region was selected, and named pRC/RSV-hAR Kozak.

Example 12

Production of Cell of the Present Invention

DNA of the plasmid pGL3-TATA-MMTV-BSD or the plasmid pGL3-MMTV-BSD produced in Example 10, and the DNA of the expression plasmid pRC/RSV-hAR Kozak of the androgen receptor produced in Example 11 were linearized, respectively, and introduced into a human-derived HeLa cell, and a cell which can be used for measuring the transcription activity of a gene receiving the transcription control by an androgen receptor was produced.

First, each of DNA of the plasmid pGL3-TATA-MMTV-BSD, DNA of the plasmid pGL3-MMTV-BSD, and DNA of the plasmid pRC/RSV-hAR Kozak was digested with Sal I.

The HeLa cell was cultured using a dish (manufactured by Falcon) having a diameter of about 10 cm in the presence of 5% $CO_2$ at 37° C. using DMEM medium containing 10% FBS (manufactured by Nissui Pharmaceutical Co., Ltd.). About $5 \times 10^5$ cells were cultured, and next day, into this cell was introduced DNAs of the above-mentioned linearized plasmids by a lipofection method using lipofectamine (manufactured by GIBCO) in the following combination: 1̂ pGL3-TATA-MMTV-BSD and pRC/RSV-hAR Kozak, 2̂ pGL3-MMTV-BSD and pRC/RSV-hAR Kozak. Conditions of the lipofection method include, according to the description of a manual appended to lipofectamine, a treating time of 5 hours, a total amount of the linearized plasmid DNAs of 7 µg (respectively 3.5 µg)/dish, and an amount of lipofectamine of 21 µl/dish. After the lipofection treatment, the medium was substituted with DMEM medium containing 10% FBS and cultured for about 36 hours. Then, the cell was removed from the dish by trypsinization and recovered, and transferred to a culturing vessel comprising a medium containing G418 added to a final concentration of 800 µg/ml and blastcidin S added in a final concentration of 16 µg/ml, and cultured for about one month while exchanging the medium with a new medium (containing the above-mentioned selective chemical) at every 3 to 4 days. The emerged cell colonies having a diameter from 1 mm to several mm were transferred respectively to a 96-well plate (manufactured by Bell Told) on which the medium had been previously separated and poured, and that was cultured further. When the cell proliferated to extent occupying half or more of the bottom surface of the well (5 days after transfer), the cell was removed by trypsinization and recovered and divided into three portions and added to three new 96-well view plates. On one plate, passage and culturing were continued, as a master plate. On one of the remaining two plates, DHT dissolved in DMSO was added to a final concentration of 10 nM, and on the other plate, DMSO of the same volume as that of the above-mentioned DHT solution was added, and both of them were cultured for 2 days. Then, in these two plates, the medium was removed from the well, cells adhered to vessel walls were washed with PBS(−) twice, and PGC 50 (manufactured by Toyo Ink) diluted 5-fold was then added in an amount of 20 µl per well and left for 30 minutes at room temperature. These plates were set in a Luminometer LB96P (manufactured by Bell Told) equipped with an automated enzyme substrate injector, and 50 µl of a substrate solution, PGL100 (manufactured by Toyo Ink) was automatically separated and poured, and the luciferase activity was measured. A cell producing 2-fold or more higher luciferase activity in the system containing added DHT than in the system containing no added DHT was selected.

Test Example 3

Reporter Assay Using Cell of the Present Invention

A medium prepared by addition to phenol read-free MEM medium (manufactured by Nissui Pharmaceutical Co., Ltd.) of charcoal dextran-treated FBS so as to give a final concentration of 10% was used, and a cell of the present invention prepared by introducing the DNA of the plasmid pGL3-MMTV-BSD and the DNA of the plasmid pRC/RSV-hAR Kozak in Example 12 was added to a 96-well plate used for measuring luciferase light emission and for culturing (#3903, manufactured by Corning Coaster) at about $2 \times 10^4$ cells/well, and cultured overnight. Then, to this cell was added DHT dissolved in DMSO. Therein, the dissolving solution was prepared and added, so that the final concentration of DHT increased, each by 10-fold, through the respective test districts and the final DMSO amounts in the culturing solution in all of the test districts coincided at 0.1%. A control district containing only an added solvent (DMSO) was provided as a system containing no added DHT.

Figure 4:
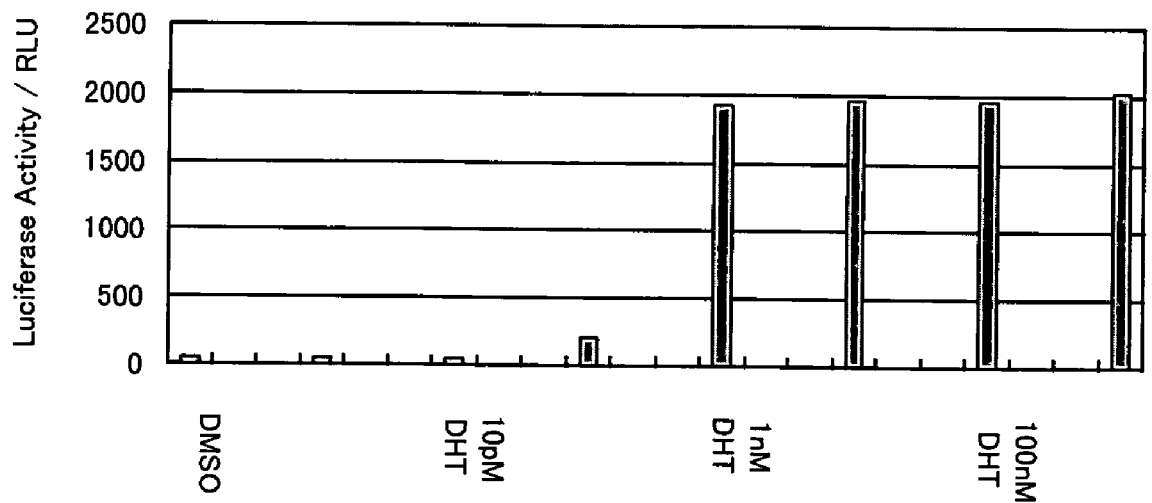
FIG. 4 is a view showing the results of a measurement of the ability of DHT to activate androgen receptor, by a reporter assay using a cell of the present invention made by introducing DNA of plasmid pGL3-MMTV-BSD and DNA of plasmid pRC/RSV-hAR Kozak. Columns show, from left side, an area in which only DMSO, which is used as a solvent for DHT, is added (DMSO), an area in which DHT is added to a final concentration of 1 pM, an area in which DHT is added to a final concentration of 10 pM (10 pM DHT), an area in which DHT is added to a final concentration of 100 pM, an area in which DHT is added to a final concentration of 1 nM (1 nM DHT), an area in which DHT is added to a final concentration of 10 nM, an area in which DHT is added to a final concentration of 100 nM (100 nM DHT), and an area in which DHT is added to a final concentration of 1 pM.

These cells were cultured, and the medium was removed 36 hours after the addition of DHT, and the cell was washed twice with PBS (−), and PGC 50 (manufactured by Toyo Ink) diluted 5-fold was then added in an amount of 20 μl per well, and left for 30 minutes at room temperature. This plate was set in a Luminometer LB96P (manufactured by Bell Told) equipped with an automated enzyme substrate injector, and 50 μl of a substrate solution PGL100 (manufactured by Toyo Ink) was automatically separated and poured, and the luciferase activity was measured. The results are shown in FIG. 4. Increase in luciferase activity along with increase in the concentration of DHT added to the cell was recognized, in the cell of the present invention for measuring the transcription activity of a gene receiving the transcription control of androgen receptor.

In the same manner as described above, the agonist activity of a chemical substance on an addrogen receptor can be measured by adding a chemical substance instead of DHT to each test district and conducting the above-mentioned test in a similar manner.

On the other hand, the antagonist activity of a chemical substance on the intended androgen receptor can be measured by adding, together with a chemical substance, DHT to each test district so as to give a concentration around $EC_{50}$ value, and conducting a test similar to as described above.

Example 13

Production of DNA (Plasmid) Comprising in a Molecule, the Ligand-Responsive Reporter Gene and the Selective Marker Gene)

An oligonucleotide comprising a nucleotide sequence (5'-CAAGGGGATCCAGCTTGACCTGACGT-CAGGTCAAGTCG-3') containing a recognition sequence (TRE) of a thyroid receptor, and an oligonucleotide comprising a nucleotide sequence complimentary to the aforementioned nucleotide sequence were synthesized by a DNA synthesizer, and the products were annealed to obtain a double-stranded DNA (hereinafter, referred to as TRE DNA), and a T4 ligase was reacted with the DNA to allow the double-stranded DNA to bond in tandem, and T4 polynucleotide kinase was allowed to act on this to phosphorylate both ends thereof.

Two oligonucleotides; 5'-GATCTCGACTATAAA-GAGGGCAGGCTGTCCTCTAAGCGTCACCACGACT TCA-3' and 5'-AGCTTGAAGTCGTGGTGACGCTTA-GAGGACAGCCTGCCCTCTTTATAGT CGA-3' having a nucleotide sequences derived from a nucleotide sequence near the TATA box of a mouse metallothionein I gene and the leader sequence were annealed to obtain a double stranded DNA, and T4 polynucleotide kinase was allowed to act on this to phosphorylate both ends thereof (hereinafter, this DNA is referred to as TATA DNA). On the other hand, a plasmid pGL3 (manufactured by Promega) containing a fire fly luciferase gene was digested with restriction enzymes Bgl II and Hind III, to this was further added Bacterial alkaline phosphatase (BAP) and the mixture was kept at 65° C. for 1 hour. Then, this incubated solution was subjected to electrophoresis using an agarose having a low melting point (Agarose L; manufactured by Nippon Gene), and DNA was recovered from gel of the band portion. About 100 ng of this DNA and 1 μg of the above-mentioned TATA DNA were mixed and bonded via a T4 ligase to produce a plasmid pGL3-TATA.

Then, pGL3-TATA was digested with a restriction enzyme Sma I, to this was further added BAP, and the mixture was kept at 65° C. for 1 hour. This incubated solution was subjected to electrophoresis using agarose gel having a low melting point, and the DNA was recovered from the gel of the band portion. About 100 ng of this DNA and about 1 μg of the above-mentioned TRE DNA which had been bonded in tandem and of which ends had been phosphorylated were mixed and reacted with a T4 ligase, and the reaction solution was introduced into a E. coli DH5α competent cell (manufactured by TOYOBO). The DNA of the respective plasmids contained in several colonies of E. coli which showed ampicillin resistance were purified and were digested with restriction enzymes Kpn I and Xho I and the digested solution was analyzed by agarose gel electrophoresis. A plasmid having a structure in which 5 copies of TRE DNAs had been introduced in tandem into the Sma I site of pGL3-TATA was selected, and named plasmid pGL3-TATA-TRE×5.

Then, this pGL3-TATA-TRE×5 was digested with Sal I, then, the ends thereof were blunted with Blunting kit (manufactured by Takara Shuzo Co., Ltd.). Separately, Blastcidin S deaminase gene-expressing cassette (Bam HI-Bam HI fragment) derived from pUCSV-BSD (purchased from FUNA-KOSHI) was blunted in a similar manner and was bonded via a T4 ligase to the above-mentioned blunted plasmid, and that was introduced into an E. coli DH5α competent cell. The DNA were isolated from the resulting E. coli clones which showed ampicillin resistance, to obtain a plasmid, named pGL3-TATA-TRE×5-BSD, having a structure in which a blastcidin S deaminase gene-expressing cassette had been introduced into the blunted Bam HI site.

Example 14

Production of Ligand-Responsive Transcription Control Factor-Expressing Plasmid (1) Thyroid Hormone Receptor a Expression Plasmid A forward primer: 5'-TGGAATTGAAGTGAATGGAA-CAGAAGCCAAGCAAGGT-3' and a reverse primer: 5'-TG-GCCGCCTGAGGCTTTAGACTTCCTGATCCTCAA-3' were designed, based on the nucleotide sequence of a thyorid hormone receptor α gene published under Genbank Accession No. M24748, and synthesized by a DNA synthesizer (Model 394 manufactured by Applied Biosystems), to obtain cDNA coding a human thyroid hormone receptor α.

Then, the above-mentioned primers each in an amount of 10 pmol were added to 10 ng of human hepatic cDNA (Quick clone cDNA# 7113 manufactured by Clone Tech) as a template, and a PCR reaction was conducted using a LA-Taq polymerase (manufactured by Takara Shuzo Co., Ltd.) and a buffer appended with the enzyme, in a reaction solution amount of 50 µl. In this reaction, the reaction solution was kept at 95° C. for 1 minute and then kept at 68° C. for three minutes, and this cycle was repeated 35-times, using a PCR system 9700 (manufactured by Applied Biosystems). Then, the whole reaction solution was subjected to agarose gel electrophoresis using an agarose having a low melting point (Agarose L; manufactured by Nippon Gene). That the band having a size expected from the known sequence had been amplified was confirmed, and DNA was recovered from the band, and a sample for direct sequence was prepared using this DNA and Die Terminator Sequence kit FS (manufactured by Applied Biosystems). This was subjected to nucleotide sequence analysis using an Auto Sequencer (Model 377 manufactured by Applied Biosystems), to confirm the nucleotide sequence.

PCR using a forward primer: 5'-CCCAGCCACCATG-GAACAGAAGCCAAGCAAGGTGGAGTGT-3' and a reverse primer: 5'-TGGCCGCCTGAGGCTTTAGACTTC-CTGATCCTCAA-3' was conducted by using as a template about 100 ng of the DNA obtained as described above, to prepare a DNA containing a Kozak consensus sequence directly before the translation initiation codon ATG of a thyroid hormone receptor α gene. Namely, 0.1 µg of thyroid hormone receptor α cDNA as a template, LA-Taq polymerase (manufactured by Takara Shuzo Co., Ltd.), reaction buffer appended with the enzyme, and the above-mentioned primers each in 10 pmol were mixed to obtain a reaction solution in an amount of 50 µl, and the solution was kept at 95° C. for 1 minute and then kept at 68° C. for 3 minutes, and this cycle was repeated 20-times. The thus amplified product thus obtained was separated and recovered by a low temperature agarose gel electrophoresis method. Then, about 1 µg of this product was treated with a DNA Blunting kit (manufactured by Takara Shuzo Co., Ltd.) to blunt the ends thereof, which were reacted with T4 polynucleotide kinase for phosphorylation of the ends thereof. This DNA was treated with phenol and purified by an ethanol precipitation method, and the whole purified product was used as an insert DNA for producing an expression plasmid.

A pRC/RSV (manufactured by Invitrogen) containing a RSV promoter and a neomycin-resistant gene was digested with a restriction enzyme Hind III, to this was further added BAP and the mixture was kept at 65° C. for 1 hour. Then this was purified by treatment with phenol and precipitation with ethanol, and the ends thereof were blunted by treating with a Blunting kit (manufactured by Takara Shuzo Co., Ltd.), and that was subjected to agarose gel electrophoresis using an agarose having a low melting temperature (Agarose L, manufactured by Nippon Gene), and DNA was recovered from the band portion. About 100 ng of the recovered vector DNA and the whole amount of the above-mentioned inserted DNA were mixed, to this was added a T4 ligase and they were reacted. This reaction solution was introduced into an *E. coli* DH5α competent cell, and the plasmid DNA was prepared from a colony showing ampicillin-resistance, and the nucleotide sequence thereof was determined by a die terminator method using an ABI model 377 type Auto Sequencer. The resulting nucleotide sequence was compared with a nucleotide sequence obtained in the above-mentioned direct sequence, and a plasmid providing confirmation of complete accordance between the nucleotide sequences in the translation region was selected, and named pRC/RSV-hTRα Kozak.

(2) Thyroid Hormone Receptor β Expression Plasmid

A forward primer: 5'-TTACTAACCTATAACCCCCAA-CAGTATGACAGAAA-3' and a reverse primer: 5'-CAGTCTAATCCTCGAACACTTCCAGGAA-CAAAGGG-3' were designed, based on the nucleotide sequence of a thyorid hormone receptor β gene published under Genbank Accession No. M26747, and synthesized by a DNA synthesizer (Model 394 manufactured by Applied Biosystems), to obtain cDNA coding a human thyroid hormone receptor β.

Then, the above-mentioned primers each in an amount of 10 pmol were added to 10 ng of a human hepatic cDNA (Quick clone cDNA# 7113 manufactured by Clone Tech) as a template, and a PCR reaction was conducted using a LA-Taq polymerase (manufactured by Takara Shuzo Co., Ltd.) and a buffer appended with the enzyme, in a reaction solution amount of 50 µl. In this reaction, the reaction solution was kept at 95° C. for 1 minute and then kept at 68° C. for three minutes, and this cycle was repeated 35-times, using a PCR system 9700 (manufactured by Applied Biosystems). Then, the whole reaction solution was subjected to agarose gel electrophoresis using an agarose having a low melting point (Agarose L; manufactured by Nippon Gene). That the band having a size expected from the known sequence had been amplified was confirmed, and then the DNA was recovered from the band, and a sample for direct sequence was prepared using this DNA and Die Terminator Sequence kit FS (manufactured by Applied Biosystems). This was subjected to nucleotide sequence analysis using an Auto Sequencer (Model 377 manufactured by Applied Biosystems), to confirm the nucleotide sequence.

PCR using a forward primer: 5'-CCCAGCCACCATGA-CAGAAAATGGCCTTACAGCTTGGGAC-3' and a reverse primer: 5'-CAGTCTAATCCTCGAACACTTCCAGGAA-CAAAGGG-3' was conducted using as a template about 100 ng of the DNA obtained as described above, to prepare DNA containing a Kozak consensus sequence directly before the translation initiation codon ATG of a thyroid hormone receptor α gene. Namely, 0.1 µg of a thyoroid hormone receptor βcDNA as a template, LA-Taq polymerase (manufactured by Takara Shuzo Co., Ltd.), reaction buffer appended with the enzyme, and the above-mentioned primers each in 10 pmol were mixed to obtain a reaction solution in an amount of 50 µl, and the solution was kept at 95° C. for 1 minute and then kept at 68° C. for 3 minutes, and this cycle was repeated 20-times. The thus amplified product thus obtained was separated and recovered by a low temperature agarose gel electrophoresis method. Then, about 1 µg of this product was treated with DNA Blunting kit (manufactured by Takara Shuzo Co., Ltd.) to blunt the ends thereof and were reacted with T4 polynucleotide kinase for phosphorylation of the ends thereof. This DNA was treated with phenol and was purified by an ethanol precipitation method, and the whole purified product was used as insert DNA for producing an expression plasmid.

A pRC/RSV (manufactured by Invitrogen) containing a RSV promoter and a neomycin-resistant gene was digested with a restriction enzyme Hind III, then, to this was further added BAP and the mixture was kept at 65° C. for 1 hour. Then this was purified by treatment with phenol and precipitation with ethanol, and the ends thereof were blunted by treating with a Blunting kit (manufactured by Takara Shuzo Co., Ltd.), and subjected to agarose gel electrophoresis using an agarose having a low melting temperature (Agarose L, manufactured by Nippon Gene), and the DNA was recovered from the band portion. About 100 ng of the recovered vector DNA and the whole amount of the above-mentioned isocyanate were mixed, to this was added a T4 ligase and they were reacted. This reaction solution was introduced into an *E. coli* DH5α competent cell, and the plasmid DNA was then prepared from a colony showing ampicillin-resistance, and the nucleotide sequence thereof was determined by a die terminator method using an ABI model 377 type Auto Sequencer. The resulting nucleotide sequence was compared with a nucleotide sequence obtained in the above-mentioned direct sequence, and a plasmid providing confirmation of complete accordance between nucleotide sequences in the translation region was selected, and named pRC/RSV-hTRβ Kozak.

Example 15

Production of Cell of the Present Invention (1) Thyroid Hormone Receptor α

The DNA of the plasmid pGL3-TATA-TREx5-BSD produced in Example 1 and the DNA of the expression plasmid pRC/RSV-hTRα Kozak of thyroid hormone receptor a produced in Example 2 were linearized, respectively, and introduced into a human-derived HeLa cell, and a cell which can be used for measuring the transcription activity of a gene receiving the transcription control by a thyroid hormone a receptor was produced.

First, DNA of the plasmid pGL3-TATA-TREx5-BSD was digested with Not I, and DNA of the plasmid pRC/RSV-hTRα Kozak was digested with Sal I.

The HeLa cell was cultured by using a dish (manufactured by Falcon) having a diameter of about 10 cm in the presence of 5% $CO_2$ at 37° C., using DMEM medium containing 10% FBS (manufactured by Nissui Pharmaceutical Co., Ltd.). About $5\times10^5$ cells were cultured, and next day, into this cell were introduced simultaneously DNA of the plasmid pGL3-TATA-TREx5-BSD and DNA of the plasmid pRC/RSV-hTRα Kozak, each linearized as described above, by a lipofection method using lipofectamine (manufactured by GIBCO). Conditions of the lipofection method include, according to the description of a manual appended to lipofectamine, a treating time of 5 hours, a total amount of the linearized plasmid DNAs of 7 μg (respectively 3.5 μg)/dish, and an amount of lipofectamine of 21 μl/dish. After the lipofection treatment, the medium was substituted with DMEM medium containing 10% FBS and cultured for about 36 hours. Then, the cell was removed from the dish by trypsinization and recovered, and transferred to a culturing vessel comprising a medium containing G418 added to a final concentration of 800 μg/ml and blastcidin S added to a final concentration of 16 μg/ml, and was cultured for about one month while exchanging the medium with a new medium (containing the above-mentioned selective chemical) at every 3 to 4 days. The emerged cell colonies having a diameter from 1 mm to several mm were transferred respectively to a 96-well plate (manufactured by Bell Told) to which the medium had been previously separated and poured, and that was cultured further. When the cell proliferated to an extent of occupying half or more of the bottom surface of the well (5 days after transfer), the cell was removed by trypsinization and recovered, and divided into three portions and added to three new 96-well view plates. On one plate, passage and culturing were continued, as a master plate. On one of the remaining two plates, T3 dissolved in DMSO was added to a final concentration of 1 μM, and on the other plate, DMSO of the same volume as that of the above-mentioned T3 solution was added, and both of them were cultured for 2 days. Then, in these two plates, the medium was removed from the well, cells adhered to vessel walls were washed with PBS(−) twice, and PGC 50 (manufactured by Toyo Ink) diluted 5-fold was added in an amount of 20 μl per well, and left for 30 minutes at room temperature. These plates were set in a Luminometer LB96P (manufactured by Bell Told) equipped with an automated enzyme substrate injector, and 50 μl of a substrate solution PGL100 (manufactured by Toyo Ink) was automatically separated and poured, and the luciferase activity was measured. A cell providing 2-fold or more higher luciferase activity in the system containing added T3 than in the system containing no added T3 was selected.

(2) Thyroid Hormone Receptor β

The DNA of the plasmid pGL3-TATA-TREx5-BSD produced in Example 1 and the DNA of the expression plasmid pRC/RSV-hTRβ Kozak of the thyroid hormone receptor β produced in Example 2 were linearized, respectively, and introduced into a human-derived HeLa cell, and a cell which can be used for measuring the transcription activity of a gene receiving the transcription control by a thyroid hormone receptor β was produced.

First, DNA of the plasmid pGL3-TATA-TREx5-BSD was digested with Not I, and DNA of the plasmid pRC/RSV-hTRβ Kozak was digested with Sal I.

The HeLa cell was cultured using a dish (manufactured by Falcon) having a diameter of about 10 cm in the presence of 5% $CO_2$ at 37° C., using DMEM medium containing 10% FBS (manufactured by Nissui Pharmaceutical Co., Ltd.). About $5\times10^5$ cells were cultured, and next day, into this cell were introduced simultaneously DNA of the plasmid pGL3-TATA-TREx5-BSD and DNA of the plasmid pRC/RSV-hTRβ Kozak, each linearized as described above, by a lipofection method using lipofectainine (manufactured by GIBCO). Conditions of the lipofection method include, according to the description of the manual appended to lipofectamine, a treating time of 5 hours, a total amount of the linearized plasmid DNAs of 7 μg (respectively 3.5 μg)/dish and an amount of lipofectamine of 21 μl/dish. After the lipofection treatment, the medium was substituted with DMEM medium containing 10% FBS and cultured for about 36 hours. Then, the cell was removed from the dish by trypsinization and recovered and transferred to a culturing vessel comprising a medium containing G418 added to a final concentration of 800 μg/ml and blastcidin S added to a final concentration of 16 μg/ml, and cultured for about one month while exchanging the medium by a new medium (containing the above-mentioned selective chemical) at every 3 to 4 days. The emerged cell colonies having a diameter from 1 mm to several mm were transferred respectively to a 96-well plate (manufactured by Bell Told) to which the medium had been previously separated and poured, that was and cultured further. When the cell proliferated to the extent of occupying half or more of the bottom surface of the well (5 days after transfer), the cell was removed by trypsinization and recovered, and divided into three portions and added to three new 96-well view plates. On one plate, passage and culturing were continued, as a master plate. On one of the remaining two plates, T3 dissolved in DMSO was added to a final concentration of 1 μM, and on the other plate, DMSO of the same volume as that of the above-mentioned T3 solution was added, and both of them were cultured for 2 days. Then, in these two plates, the medium was removed from the well, cells adhered to vessel walls were washed with PBS(−) twice, and PGC 50 (manufactured by Toyo Ink) diluted 5-fold was then added in an amount of 20 μl per well, and left for 30 minutes at room temperature. These plates were set in a Luminometer LB96P (manufactured by Bell Told) equipped with an automated enzyme substrate injector, and 50 μl of a substrate solution, PGL100 (manufactured by Toyo Ink) was automatically separated and poured, and luciferase activity was measured. A cell providing 2-fold or more higher luciferase activity in the system containing added T3 added than in the system containing no added T3 was selected.

Test Example 4

Reporter Assay Using Cell of the Present Invention

A medium prepared by addition to phenol read-free MEM medium (manufactured by Nissui Pharmaceutical Co., Ltd.) of charcoal dextran-treated FBS so as to give a final concentration of 10% was used, and a cell of the present invention prepared as described in Example 15 was added to a 96-well plate used for measuring luciferase light emission and for culturing (#3903, manufactured by Corning Coaster) at about $2 \times 10^4$ cells/well, and that was cultured overnight. Then, to this cell was added T3 dissolved in DMSO. Therein, the dissolving solution was prepared and added, so that the final concentration of T3 increased, each by 10-fold, through the respective test districts and the final DMSO amounts in the culturing solution in all of the test districts coincided at 0.1%. A control district containing only an added solvent (DMSO) was provided as a system containing no added T3.

Figure 5:
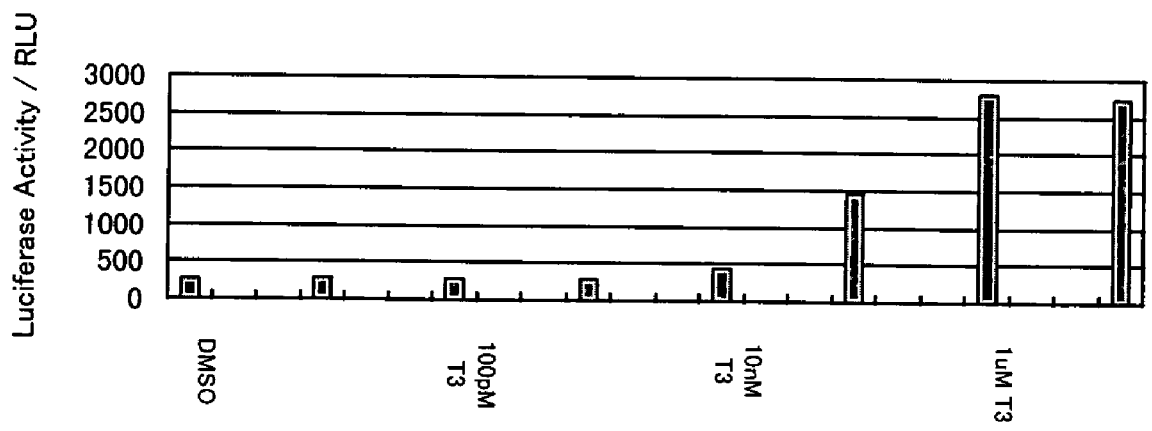
FIG. 5 is a view showing the results of a measurement of the ability of T3 to activate thyroid hormone receptor α, by a reporter assay using a cell of the present invention. Columns show, from left side, an area in which only DMSO used as a solvent for T3 is added (DMSO), an area in which T3 is added to a final concentration of 10 pM, an area in which T3 is added to a final concentration of 100 pM (100 pM T3), an area in which T3 is added to a final concentration of 1 nM, an area in which T3 is added to a final concentration of 10 nM (10 nM T3), an area in which T3 is added to a final concentration of 100 nM, an area in which T3 is added to a final concentration of 1 μM (1 μM T3), and an area in which T3 is added to a final concentration of 10 μM.
Figure 6:
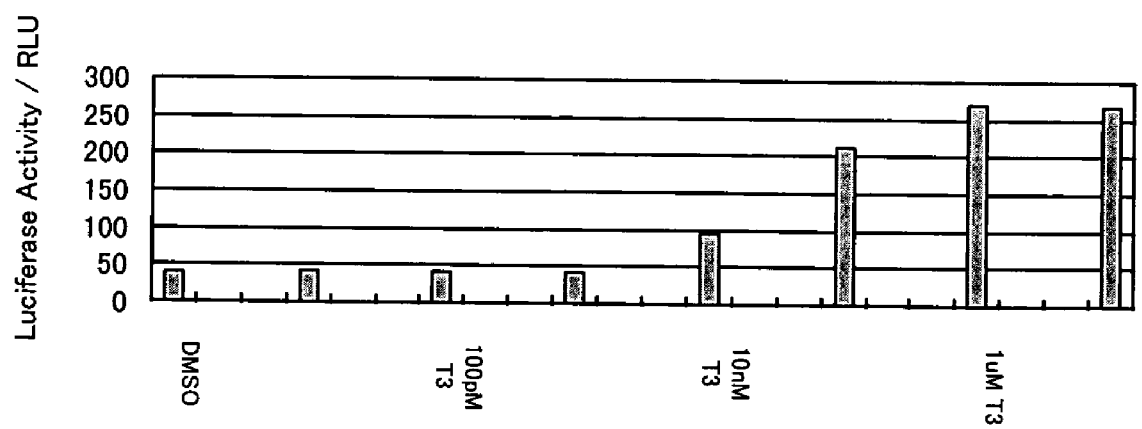
FIG. 6 is a view showing the results of a measurement of the ability of T3 to activate thyroid hormone receptor β, by a reporter assay using a cell of the present invention. Columns show, from left side, an area in which only DMSO, which is used as a solvent for T3, is added (DMSO), an area in which T3 is added to a final concentration of 10 pM, an area in which T3 is added to a final concentration of 100 pM (100 pM T3), an area in which T3 is added to a final concentration of 1 nm, an area in which T3 is added to a final concentration of 10 nM (10 mM T3), an area in which T3 is added to a final concentration of 100 nM, an area in which T3 is added to a final concentration of 1 μM (1 μMT3), and an area in which T3 is added to a final concentration of 10 μM.

These cells were cultured, and the medium was removed 36 hours after the addition of T3, and the cell was washed twice with PBS (−), and then PGC 50 (manufactured by Toyo Ink) diluted 5-fold was added in an amount of 20 μl per well, and left for 30 minutes at room temperature. This plate was set in a Luminometer LB96P (manufactured by Bell Told) equipped with an automated enzyme substrate injector, and 50 μl of a substrate solution PGL100 (manufactured by Toyo Ink) was automatically separated and poured, and the luciferase activity was measured. The results are shown in FIG. 5 and FIG. 6. Increase in luciferase activity along with increase in the concentration of T3 added to the cell was recognized, in both the cell of the present invention for measuring the transcription activity of a gene receiving the transcription control of thyroid hormone receptor α and the cell of the present invention for measuring the transcription activity of a gene receiving the transcription control of thyroid hormone receptor β.

In the same manner as described above, the agonist activity of a chemical substance on the intended thyroid hormone receptor can be measured by adding the chemical substance to each test district instead of T3 and conducting the above-mentioned test in a similar manner.

On the other hand, the antagonist activity of the chemical substance on the intended thyroid hormone receptor can be measured, by adding, together with the chemical substance, T3 so as to give a concentration around $EC_{50}$, to each test district and conducting the test in a similar manner as described above.

According to the present invention, it is possible to provide a cell which can be used for evaluating the action of a chemical substance over the transcription control ability of a ligand-responsive transcription control factor.

What is claimed is:

1. An animal cell in vitro expressing a ligand-responsive transcription control factor and stably transformed with a DNA comprising in a molecule, both of the following polynucleotides (a) and (b):
   (a) a polynucleotide comprising a reporter protein coding region connected functionally downstream from a transcription control region, wherein said transcription control region
      (a-1) substantially consists of a recognition sequence of said ligand-responsive transcription control factor and a minimum promoter comprising the nucleotide sequence of SEQ ID NO: 5 which can function in said cell, and
      (a-2) contains no functional elements relating to transcription control in said cell other than the recognition sequence and the minimum promoter; and
   (b) a polynucleotide comprising a selective marker protein coding region connected functionally downstream of a promoter which can function in said cell, wherein said selective marker protein is a protein which can provide the cell with a resistance against chemicals suppressing or disturbing proliferation of the cell;
   wherein said ligand-responsive transcription control factor is one selected from among an aryl hydrocarbon receptor, estrogen receptor, androgen receptor and thyroid hormone receptor.

2. The cell according to claim 1, wherein said ligand-responsive transcription control factor is an aryl hydrocarbon receptor.

3. The cell according to claim 1, wherein said ligand-responsive transcription control factor is an estrogen receptor.

4. The cell according to claim 1, wherein said ligand-responsive transcription control factor is an androgen receptor.

5. The cell according to claim 1, wherein said ligand-responsive transcription control factor is a thyroid hormone receptor.

6. An animal cell in vitro expressing an aryl hydrocarbon receptor and an Arnt receptor, and stably transformed with a DNA comprising in a molecule, both of the following polynucleotides (a) and (b):
   (a) a polynucleotide comprising a reporter protein coding region connected functionally downstream from a transcription control region, wherein said transcription control region
      (a-1) substantially consists of a recognition sequence of said aryl hydrocarbon receptor and a minimum promoter comprising the nucleotide sequence of SEQ ID NO: 5 which can function in said cell, and
      (a-2) contains no functional elements relating to transcription control in said cell other than the recognition sequence and the minimum promoter; and
   (b) a polynucleotide comprising a selective marker protein coding region connected functionally downstream of a promoter which can function in said cell, wherein said selective marker protein is a protein which can provide the cell with a resistance against chemicals suppressing or disturbing proliferation of the cell.

7. A method for evaluating a chemical substance to have agonist activity over the transcription promoting ability of a ligand-responsive transcription control factor, said method comprising:
   (i) culturing an animal cell according to any one of claims 1, 2 and 3 to 6 in the presence of the chemical substance;

(ii) measuring the expression amount of said reporter protein encoded by the polynucleotide (a) in said cell and
(iii) assessing said chemical substance to have agonist activity over the transcription promoting ability of the ligand-responsive transcription control factor when the value of expression amount of said reporter protein as measured in step (i) is larger than a value of expression amount of said reporter protein as measured in said cell cultured in the absence of said chemical substance;
wherein said ligand-responsive transcription control factor is one selected from among an aryl hydrocarbon receptor, estrogen receptor, androgen receptor, and thyroid hormone receptor, and expressed in said cell.

8. A method for evaluating a chemical substance to have antagonist activity over the transcription promoting ability of a ligand-responsive transcription control factor, said method comprising:
(i) culturing an animal cell according to any one of claims 1, 2 and 3 to 6 in the presence of the chemical substance and a ligand of said ligand-responsive transcription control factor;
(ii) measuring the expression amount of reporter protein encoded by the polynucleotide (a) in said cell and
(iii) assessing said chemical substance to have antagonist activity over the transcription promoting ability of the ligand-responsive transcription control factor when the value of expression amount of said reporter protein measured in step (ii) is smaller than a value of expression amount of said reporter protein as measured in said cell cultured in the presence of said ligand and the absence of said chemical substance;
wherein said ligand-responsive transcription control factor is one selected from among an aryl hydrocarbon receptor, estrogen receptor, androgen receptor and thyroid hormone receptor, and expressed in said cell.

9. A measuring kit comprising an animal cell according to any one of claims 1, 2 and 3 to 6.

10. A method for obtaining an animal cell for measuring the ability to control the activity of a ligand-responsive transcription control factor, said method comprising:
(i) introducing into an animal cell, a DNA comprising in a molecule both of the following polynucleotides (a) and (b):
(a) a polynucleotide comprising a reporter protein coding region connected functionally downstream from a transcription control region, wherein said transcription control region (a-1) substantially consists of a recognition sequence of said ligand-responsive transcription control factor and a minimum promoter comprising the nucleotide sequence of SEQ ID NO: 5 which can function in said cell, and
(a-2) contains no functional elements relating to transcription control in said cell other than the recognition sequence and the minimum promoter; and
(b) a polynucleotide comprising a selective marker protein coding region connected functionally downstream of a promoter which can function in said cell, wherein said selective marker protein is a protein which can provide the cell with a resistance against chemicals suppressing or disturbing proliferation of the cell,
wherein said ligand-responsive transcription control factor is one selected from among an aryl hydrocarbon receptor, estrogen receptor, androgen receptor and thyroid hormone receptor, and wherein said animal cell is
an animal cell into which a DNA comprising a polynucleotide that encodes the ligand-responsive transcription control factor and that is connected functionally downstream of a promoter is introduced before, after or during the same time of the step (i) or an animal cell that naturally has an ability to express the ligand-responsive transcription control factor; and
(ii) recovering from the transformed cell obtained from step (i), a transformed cell having both of the introduced DNA stably maintained therein.

11. The method according to claim 10, wherein said cell is an animal cell into which a DNA comprising a polynucleotide that encodes the ligand-responsive transcription control factor and that is connected functionally downstream of a promoter is introduced before, after or during the same time of the step (i).

12. The method according to claim 11, wherein the DNA comprising a polynucleotide that encodes the ligand-responsive transcription control factor, comprises in a molecule, a polynucleotide comprising a selective marker protein coding region connected functionally downstream of a promoter which can function in said cell and which confers a phenotype different from that of the polynucleotide (b).

13. The cell according to any one of claims 1, 2 and 3 to 6, wherein said cell is prepared by introducing said DNA into a host cell selected from among NIH 3T3 cell, MCF7 cell and HeLa cell.

* * * * *